(12) United States Patent
Qin et al.

(10) Patent No.: US 9,097,710 B2
(45) Date of Patent: Aug. 4, 2015

(54) MULTIPLEXED VOLUMETRIC BAR CHART CHIP FOR POINT OF CARE BIOMARKER AND ANALYTE QUANTITATION

(71) Applicant: The Methodist Hospital Research Institute, Houston, TX (US)

(72) Inventors: Lidong Qin, Houston, TX (US); Yujun Song, Houston, TX (US)

(73) Assignee: The Methodist Hospital Research Institute, Houston, TX (US)

( * ) Notice: Subject to any disclaimer, the term of this patent is extended or adjusted under 35 U.S.C. 154(b) by 0 days.

(21) Appl. No.: 13/834,614

(22) Filed: Mar. 15, 2013

(65) Prior Publication Data

US 2014/0106346 A1    Apr. 17, 2014

Related U.S. Application Data

(60) Provisional application No. 61/714,676, filed on Oct. 16, 2012.

(51) Int. Cl.
| | |
|---|---|
| *G01N 33/543* | (2006.01) |
| *C12Q 1/68* | (2006.01) |
| *B01L 3/00* | (2006.01) |

(52) U.S. Cl.
CPC .... *G01N 33/54306* (2013.01); *B01L 3/502738* (2013.01); *C12Q 1/6823* (2013.01); *G01N 33/54366* (2013.01); *B01L 2200/0605* (2013.01); *B01L 2300/0816* (2013.01); *B01L 2300/0867* (2013.01); *B01L 2300/0887* (2013.01); *B01L 2400/0406* (2013.01); *B01L 2400/065* (2013.01)

(58) Field of Classification Search
None
See application file for complete search history.

(56) References Cited

U.S. PATENT DOCUMENTS

| | | | |
|---|---|---|---|
| 2006/0003440 A1 | 1/2006 | Streit et al. | |
| 2007/0014695 A1 | 1/2007 | Yue et al. | |
| 2007/0026439 A1 | 2/2007 | Faulstich et al. | |
| 2008/0200342 A1 | 8/2008 | Rao et al. | |
| 2008/0248591 A1 | 10/2008 | Bauer | |
| 2009/0021728 A1 | 1/2009 | Heinz et al. | |

(Continued)

FOREIGN PATENT DOCUMENTS

| | | |
|---|---|---|
| WO | WO2010/041230 | 4/2010 |
| WO | WO2010/111265 | 9/2010 |

OTHER PUBLICATIONS

Barakat et al., Multiplexed Point-Of-Care Breast Cancer Marker Detection System, UC Davis Office of Research, 2009.

(Continued)

*Primary Examiner* — Melanie Y Brown
*Assistant Examiner* — Rebecca Martinez
(74) *Attorney, Agent, or Firm* — Pandiscio & Pandiscio

(57) ABSTRACT

Apparatus for determining the quantity of a target protein, biomarker or analyte present in a sample, comprising a top plate and a bottom plate, each comprising a plurality of recesses arranged to form a plurality of rows extending parallel to one another, and a plurality of channels extending perpendicularly to the plurality of rows of the bottom plate; wherein the top plate and the bottom plate are assembled together so that the top plate is on top of the bottom plate and the recesses of the top plate communicate with the recesses of the bottom plate so as to form a plurality of rows; and wherein at least one of the top and bottom plate is configured to slide relative to the other of the top and bottom plate in order to form a plurality of columns, with each of the columns in communication with each of the channels.

86 Claims, 31 Drawing Sheets

(56) References Cited

U.S. PATENT DOCUMENTS

| | | |
|---|---|---|
| 2009/0028755 A1 | 1/2009 | Jedrzejewski et al. |
| 2009/0060797 A1 | 3/2009 | Mathies et al. |
| 2009/0181411 A1 | 7/2009 | Battrell et al. |
| 2009/0227897 A1 | 9/2009 | Wendt et al. |
| 2009/0317836 A1 | 12/2009 | Kuhn et al. |
| 2010/0140171 A1 | 6/2010 | Heath et al. |
| 2010/0261212 A1 | 10/2010 | Soman et al. |
| 2012/0028342 A1 | 2/2012 | Ismagilov et al. |
| 2012/0264132 A1 | 10/2012 | Ismagilov et al. |
| 2012/0329038 A1 | 12/2012 | Ismagilov et al. |

OTHER PUBLICATIONS

Belder, Screening in One Sweep Using The Slipchip, Angewandte Chemie, International Edition 49, pp. 6484-6486, 2010.

Bickford et al., Evaluation Of Immunotargeted Gold Nanoshells As Rapid Diagnostic Imaging Agents For HER2-Overexpressing Breast Cancer Cells: A Time-Based Analysis, NanoBiotechnology, 2008.

Du et al., SlipChip, Lab Chip, pp. 2286-2292, 2009.

Fesenmaier, New Professor Uses Chemistry And Chemical Engineering To Make A Difference, Dec. 8, 2011.

Gohring et al., Detection Of HER2 Breast Cancer Biomarker Using The Opto-Fluidic Ring Resonator Biosensor, Sensors and Actuators B, vol. 146, pp. 226-230, 2010.

IBM Lab-on-a-Chip Performs Instant Tests for Flu, Cancer, Poison, Toxins, Apr. 18, 2012.

Kawde et al., Moving Enzyme-Linked ImmunoSorbent Assay To The Pont-Of-Care Dry-Reagent Strip Biosensors, American Journal Of Biomedical Sciences, pp. 23-32, 2010.

Li et al., User-Loaded Slipchip For Equipment-Free Multiplexed Nanoliter-Scale Experiments, American Chemical Society, pp. 106-111, Dec. 14, 2009.

Liu et al., Slip Chip for Immunoassays in Nanoliter Volumes, Analytical Chemistry, pp. 3276-3282, 2010.

McGill University, Detecting Breast Cancer's Fingerprint In A Droplet Of Blood, ScienceDaily, Apr. 5, 2012, www.sciencedaily.com/releases/2012/04/120405131634.htm.

Pla-Roca et al., Antibody Colocalization Microarray: A Scalable Technology for Multiplex Protein Analysis in Complex Samples, Molecular & Cellular Proteomics 11.4, 2012.

Qin, Qin Research, 2012.

Reed, Nanowire Sensors—A Point-Of-Care Diagnostic Device To Measure Cancer Biomarkers In Blood, Technical Insights, Frost & Sullivan.

Shen et al., Digital Isothermal Quantification Of Nucleic Acids Via Simultaneous Chemical Initiation Of Recombinase Polymerase Amplification Reactions On Slipchip, Analytical Chemistry, 2011.

Shen et al., Digital PCR On A Slip Chip, Lab Chip, vol. 10, pp. 2666-2672, 2010.

Shen et al., Nanoliter Multiplex PCR Arrays On A Slipchip, Analytical Chemistry, vol. 82, No. 11, Jun. 1, 2010, pp. 4606-4612.

Soman et al., Sensitive And Multiplexed Detection Of Proteomic Antigens Via Quantum Dot Aggregation, Nanomedicine: Nanotechnology, Biology and Medicine, 2009.

Song et al,, Multiplexed volumetric bar-chart chip for point-of-care diagnostics, Nature Communications, Dec. 18, 2012.

Stern, Label-Free Biomarker Detection From Whole Blood, Nature Nanotechnology, pp. 138-142, Feb. 2010.

VerOFy®, 2011.

Wang, Electrochemical Biosensors: Towards Point-Of-Care Cancer Diagnostics, Biosensors and Bioelectronics, vol. 21, pp. 1887-1892, 2006.

Zhu et al., Au@Pt Nanoparticle Encapsulated Target-Responsive Hydrogel With Volumetric Bar-Chart Chip Readout For Quantitative Point-Of-Care Testing, Journal of the American Chemical Society, 2014.

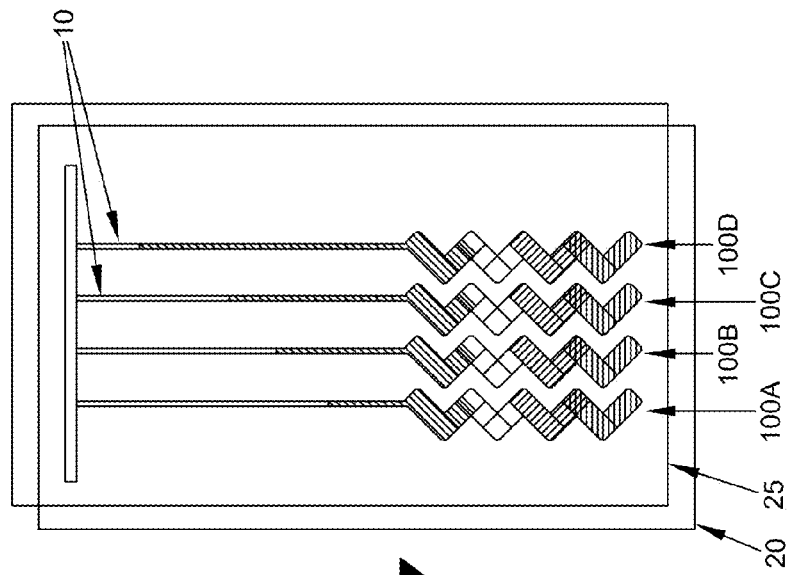
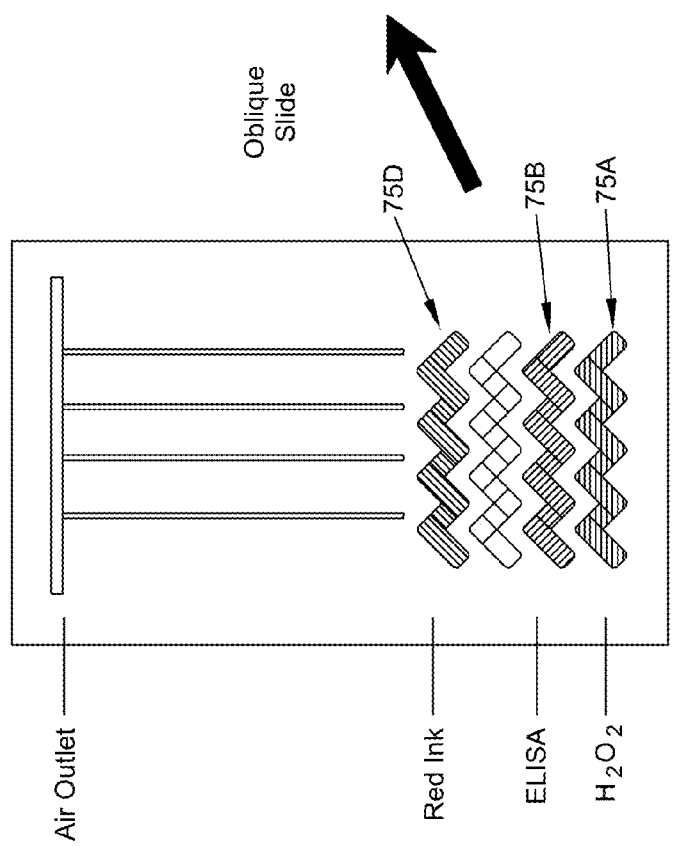
FIG. 11
FIG. 12

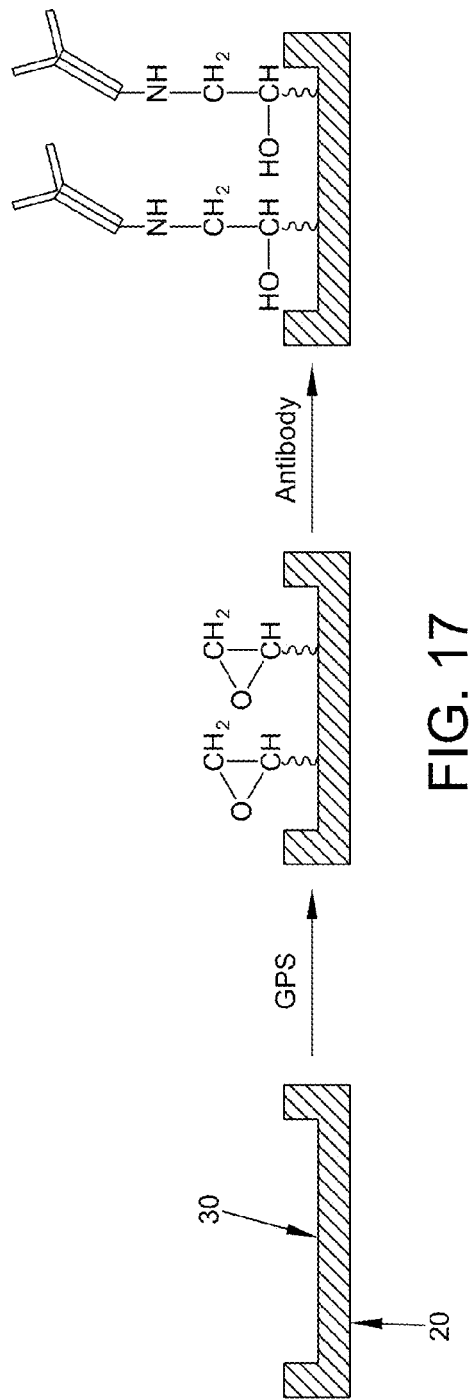
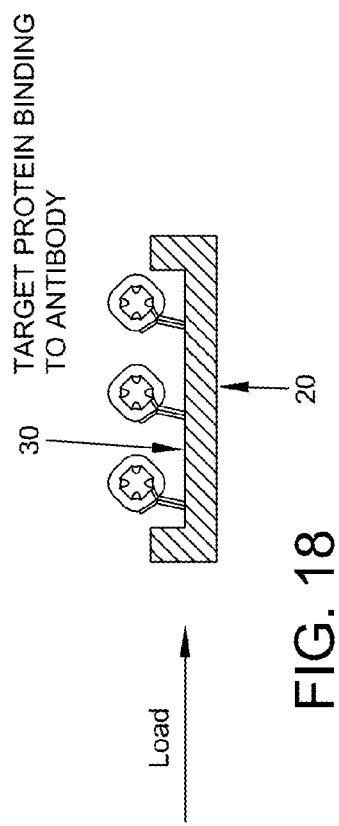
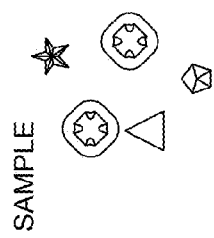
FIG. 17
FIG. 18

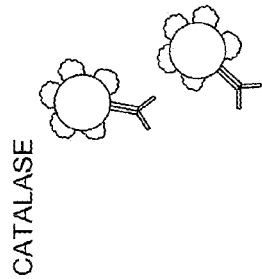
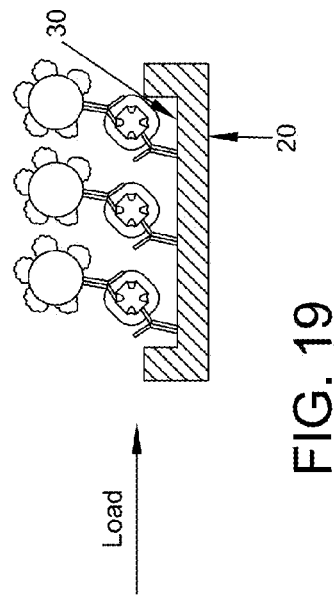
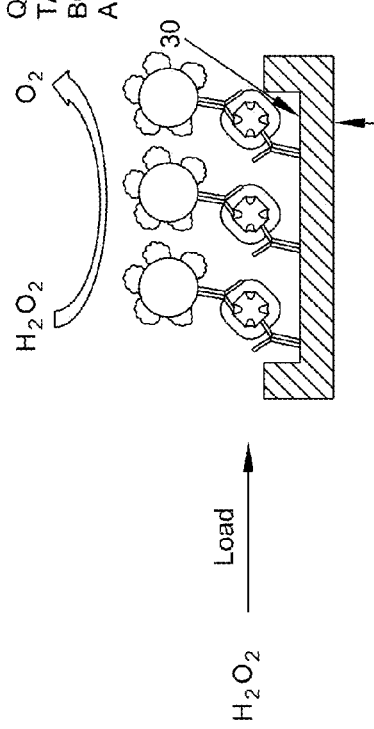
FIG. 19
FIG. 20

SCHEMATIC SERIES SHOWING THE ASSEMBLY AND OPERATION
OF THE V-CHIP ASSEMBLY

Step 1 - Plates positioned in preparation for assembly

Step 2 - Top plate begins to move over bottom plate

Step - 3 top plate continues to move over bottom plate

Step 4 - top plate continues to move over bottom plate

Step 5 - Assembly complete

Step 6 - Fill wells

Step 7 - Oblique sliding initiated

Step 8 - Oblique sliding continues

Step 9 - Oblique sliding complete, reaction begins

Step 10 - Reaction continues

Step 11 - Reaction continues

Step 712- Reaction complete, data ready to be read

Time T₁

Time T₂

Time T₃

Time T₄

Time T₅

Time T₆

Time T₇

Time T₈

Time T₉

Time T₁₀

Time T₁₁

Time T₁₂

Time T$_{13}$

MULTIPLEXED VOLUMETRIC BAR CHART CHIP FOR POINT OF CARE BIOMARKER AND ANALYTE QUANTITATION

REFERENCE TO PENDING PRIOR PATENT APPLICATION

This patent application claims benefit of prior U.S. Provisional Patent Application Ser. No. 61/714,676, filed Oct. 16, 2012 by Lidong Qin et al. for MULTIPLEXED VOLUMETRIC BAR CHART CHIP FOR POINT OF CARE BIOMARKER QUANTITATION, which patent application is hereby incorporated herein by reference.

FIELD OF THE INVENTION

This invention relates generally to methods and apparatus for determining the quantity of a protein and other biomarkers and analytes present in a sample, and more particularly to methods and apparatus for point of care determination of the quantity of a protein (and, preferably, the quantity of multiple biomarkers) present in a sample.

BACKGROUND OF THE INVENTION

Molecular quantity analysis is widely used in research, diagnosis, quality control and other types of measurements. It is well known that the diagnosis and treatment of certain medical conditions can be facilitated by identifying the presence and quantity of a selected biomarker in a sample taken from a patient. Furthermore, research has shown that, in many situations, multi-biomarker measurements can provide a more accurate diagnostic result. More particularly, biomarker research has identified many helpful proteomics and genomic panels for disease diagnosis and prognosis, including cancer, infection, cardiovascular disease, diabetes, Alzheimer's disease and others. For example, a four-biomarker panel has been developed for detecting early stage ovarian cancer, and an 18-protein biomarker panel has been developed for the diagnosis of early Alzheimer's disease.

Current methods for protein-based biomarker assays typically utilize an enzyme-linked immunosorbent assay (ELISA) approach, where the target protein binds to a specific recognition molecule, and then colorimetric, fluorescent, electrochemical or magnetic signals are introduced to transduce the binding event into a readout signal. However, inasmuch as advanced instrumentation is typically required for quantitative detection of the target protein, these methods are not ideal for point of care applications, due to the size and high cost of the instrumentation and/or the complicated operation of the instrumentation. See, for example, FIG. 1, which shows the typical approach for a protein-based biomarker assay, where a blood sample is drawn from a patient and then processed by a relatively large, complex instrument.

Thus there is a need for a new method and apparatus for point of care determination of the quantity of a protein (and, preferably, the quantity of multiple proteins) present in a sample.

SUMMARY OF THE INVENTION

These and other objects are addressed by the provision and use of a novel method and apparatus for point of care determination of the quantity of a protein (and, preferably, the quantity of multiple proteins) present in a sample.

In one form of the present invention, there is provided apparatus for determining the quantity of a target protein and other types of biomarkers or analytes present in a sample, the apparatus comprising:
  a top plate comprising a plurality of recesses arranged to form a plurality of rows extending parallel to one another; and
  a bottom plate comprising a plurality of recesses arranged to form a plurality of rows extending parallel to one another, and a plurality of channels extending perpendicularly to the plurality of rows of the bottom plate;
  wherein the top plate and the bottom plate are assembled together so that the top plate is on top of the bottom plate and the recesses of the top plate communicate with the recesses of the bottom plate so as to form a plurality of rows; and
  wherein at least one of the top plate and the bottom plate is configured to slide relative to the other of the top plate and the bottom plate in order to form a plurality of columns, with each of the plurality of columns in communication with each of the plurality of channels.

In another form of the present invention, there is provided a method for determining the quantity of a target protein and other types of biomarkers or analytes present in a sample, the method comprising:
  providing apparatus comprising:
  a top plate comprising a plurality of recesses arranged to form a plurality of rows extending parallel to one another; and
  a bottom plate comprising a plurality of recesses arranged to form a plurality of rows extending parallel to one another, and a plurality of channels extending perpendicularly to the plurality of rows of the bottom plate;
  wherein the top plate and the bottom plate are assembled together so that the top plate is on top of the bottom plate and the recesses of the top plate communicate with the recesses of the bottom plate so as to form a plurality of rows; and
  wherein at least one of the top plate and the bottom plate is configured to slide relative to the other of the top plate and the bottom plate in order to form a plurality of columns, with each of the plurality of columns in communication with each of the plurality of channels;
  binding a protein-specific antibody in at least one recess forming one of the plurality of rows of the top plate;
  positioning hydrogen peroxide in a recess adjacent to the row containing the protein-specific antibody;
  positioning ink in a recess in a row adjacent to the plurality of channels;
  positioning a sample in the at least one recess containing the protein-specific antibody;
  positioning a catalase in the at least one recess containing the protein-specific antibody and the sample;
  sliding one of the top plate and the bottom plate relative to the other of the top plate and the bottom plate so as to form the plurality of columns, with each column being in communication with one of the plurality of channels; and
  determining the quantity of the target protein and other biomarker and other molecular analyte present in the sample by detecting the longitudinal position of the ink contained in the plurality of channels.

In another form of the present invention, there is provided a method for determining the quantity of a target analyte present in a sample, the method comprising:
  providing apparatus comprising:

a top plate comprising a plurality of recesses arranged to form a plurality of rows extending parallel to one another; and a bottom plate comprising a plurality of recesses arranged to form a plurality of rows extending parallel to one another, and a plurality of channels extending perpendicularly to the plurality of rows of the bottom plate;

wherein the top plate and the bottom plate are assembled together so that the top plate is on top of the bottom plate and the recesses of the top plate communicate with the recesses of the bottom plate so as to form a plurality of rows; and wherein at least one of the top plate and the bottom plate is configured to slide relative to the other of the top plate and the bottom plate in order to form a plurality of columns, with each of the plurality of columns in communication with each of the plurality of channels;

binding a capture agent in at least one recess forming one of the plurality of rows of the top plate, introducing a sample into the at least one recess so that an analyte contained in the sample is bound to the capture agent, and binding a probe to the bound analyte; and positioning a reagent in a recess adjacent to the row containing the capture agent, bound analyte and bound probe; and positioning ink in a recess in a row adjacent to the plurality of channels;

sliding one of the top plate and the bottom plate relative to the other of the top plate and the bottom plate so as to form the plurality of columns, with each column being in communication with one of the plurality of channels; and determining the quantity of the analyte present in the sample by detecting the longitudinal position of the ink contained in the plurality of channels.

BRIEF DESCRIPTION OF THE DRAWINGS

These and other objects and features of the present invention will be more fully disclosed or rendered obvious by the following detailed description of the invention, which is to be considered together with the accompanying drawings wherein like numbers refer to like parts, and further wherein:

FIGS. 11 and 12 are schematic drawings illustrating use of the multiplexed volumetric bar chart chip of the present invention;

FIGS. 17-20 show specific steps which are performed in accordance with the method of the present invention;

DETAILED DESCRIPTION OF THE INVENTION

The present invention provides a new method and apparatus for point of care determination of the quantity of a protein (and, preferably, the quantity of multiple proteins) present in a sample.

Figure 1:
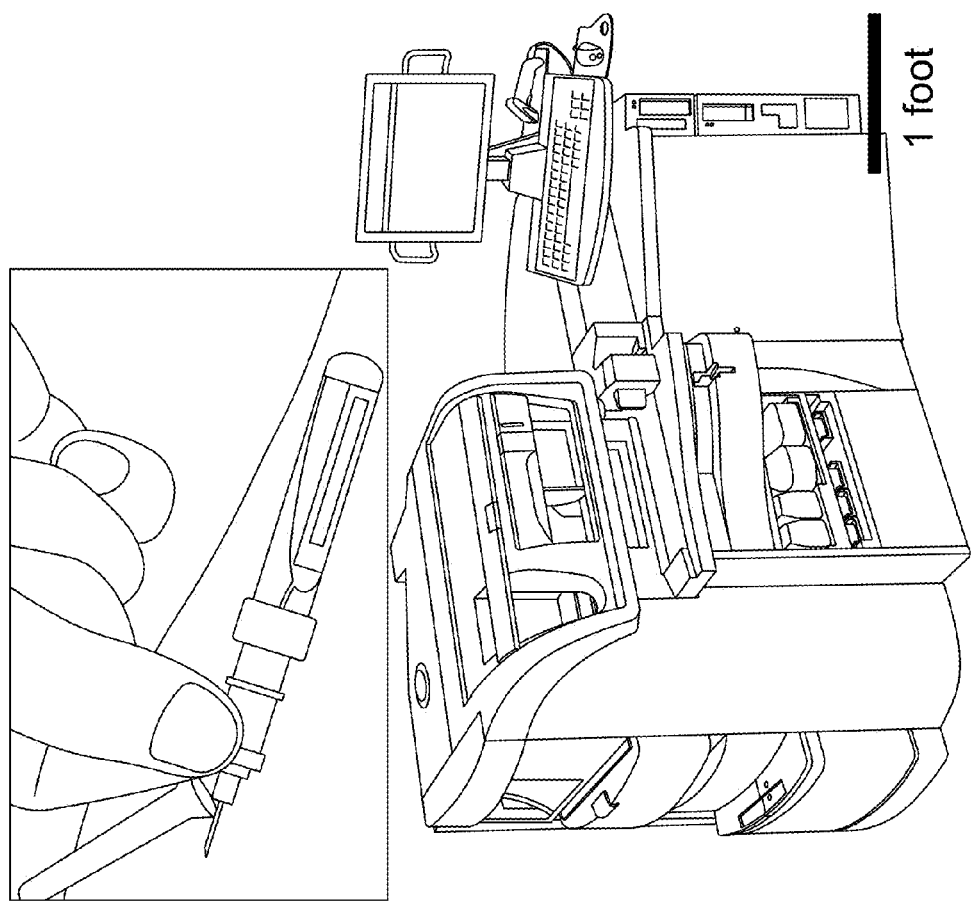
FIG. 1 which shows a typical prior art approach for a protein-based biomarker assay, where a blood sample is drawn from a patient and then processed by a relatively large, complex instrument.
Figure 2:
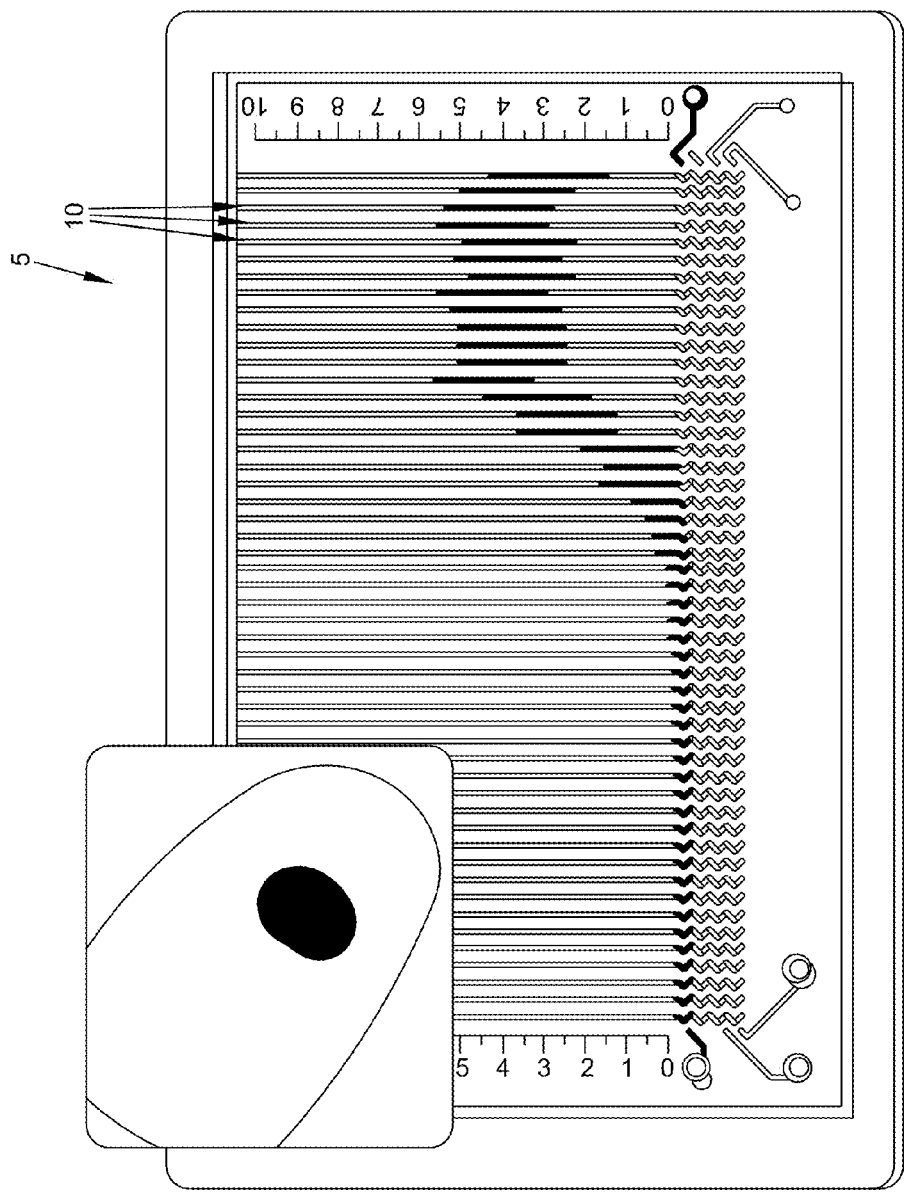
FIG. 2 shows the novel multiplexed volumetric bar chart chip of the present invention.

More particularly, and looking now at FIG. 2, in one preferred form of the invention, there is provided a novel multiplexed volumetric bar chart chip 5. Multiplexed volumetric bar chart chip 5 is configured to simultaneously determine the quantity of multiple proteins which may be present in a sample, with the quantity of each protein which is present in the sample being indicated in a particular one of a plurality of bar channels 10. By way of example but not limitation, 6, 10, 30, and 50-plexed, or more than 50-plexed, channels may be incorporated into multiplexed volumetric bar chart chip 5. Bar channels 10 may be straight (as shown in FIG. 2) or curved (e.g., serpentine, circular, z-shaped) or formed in any other configuration which provides a series of channels having a length. As a result of this construction, the review of a particular bar channel 10 will indicate the quantity of a particular protein which may be present in the sample and, significantly, the collective array of the plurality of bar channels 10 will simultaneously indicate, in bar chart form, the quantities of multiple proteins which may be present in the sample, whereby to provide multi-protein quantity measurements and hence a more comprehensive diagnostic result.

Figure 3:
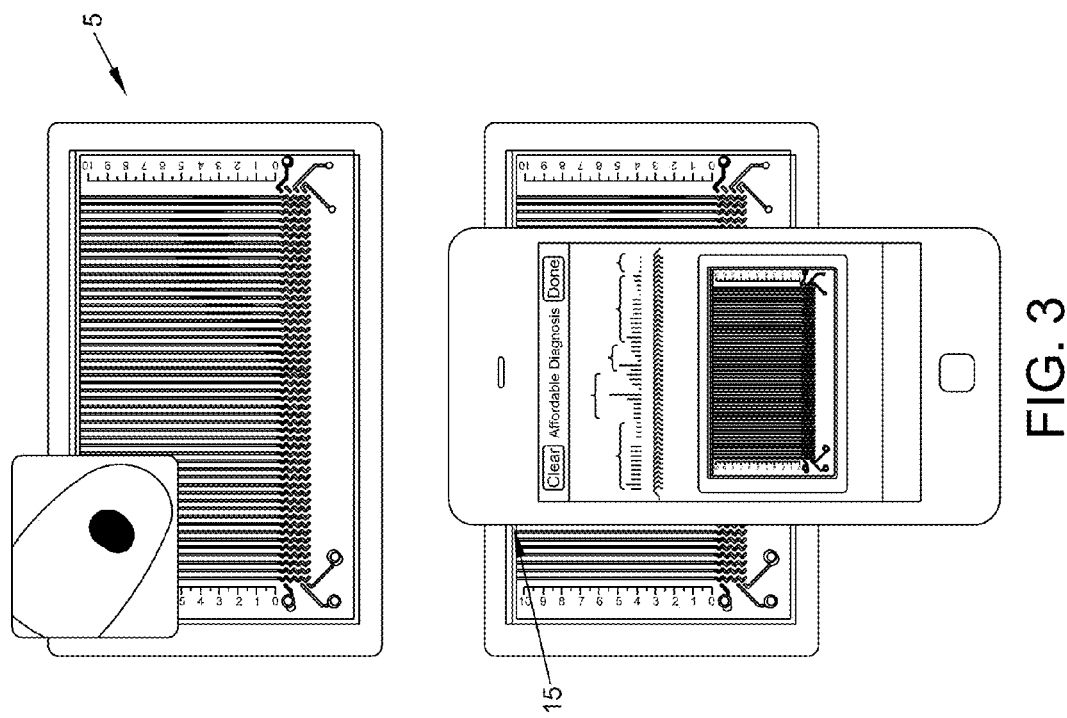
FIG. 3 shows the novel multiplexed volumetric bar chart chip of FIG. 2 and a barcode scanner which can be used to read the multiplexed volumetric bar chart chip.
Figure 4:
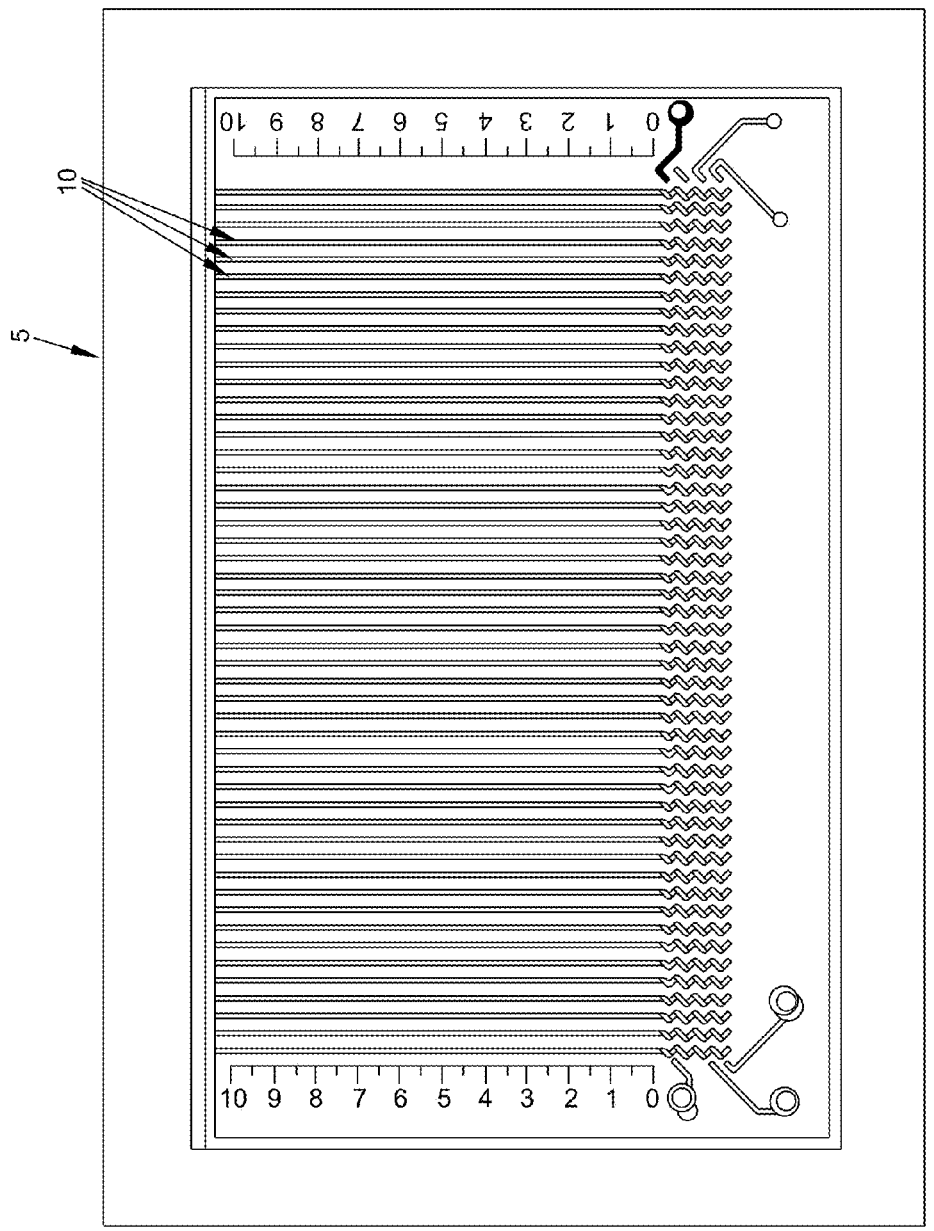
FIGS. 4-8 illustrate further details of the novel multiplexed volumetric bar chart chip of the present invention.
Figure 6:
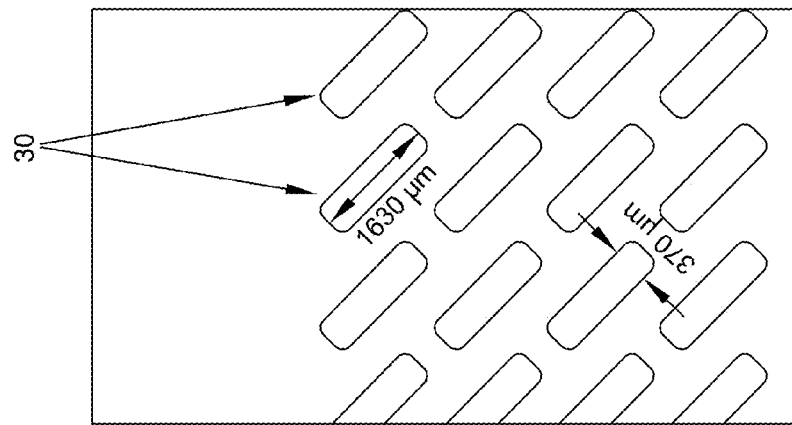
Figure 5:
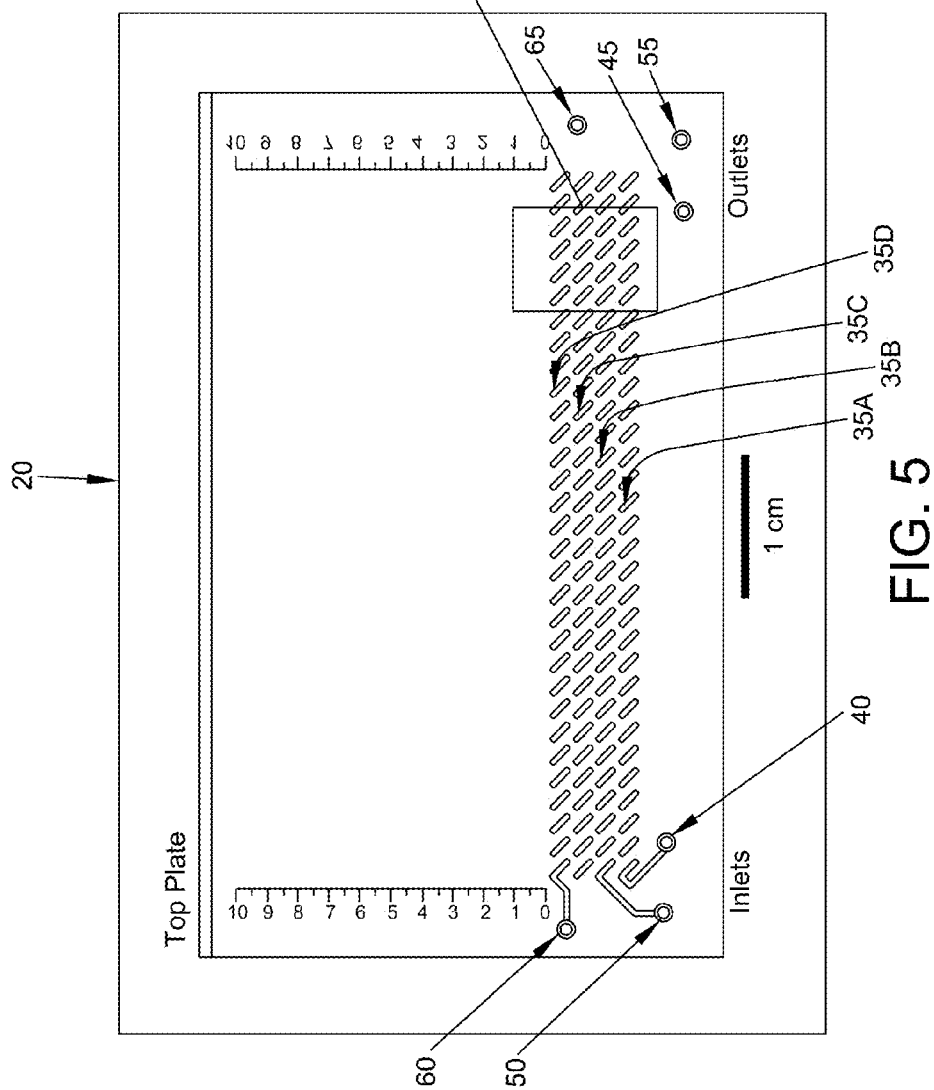
Figures 7, 8:
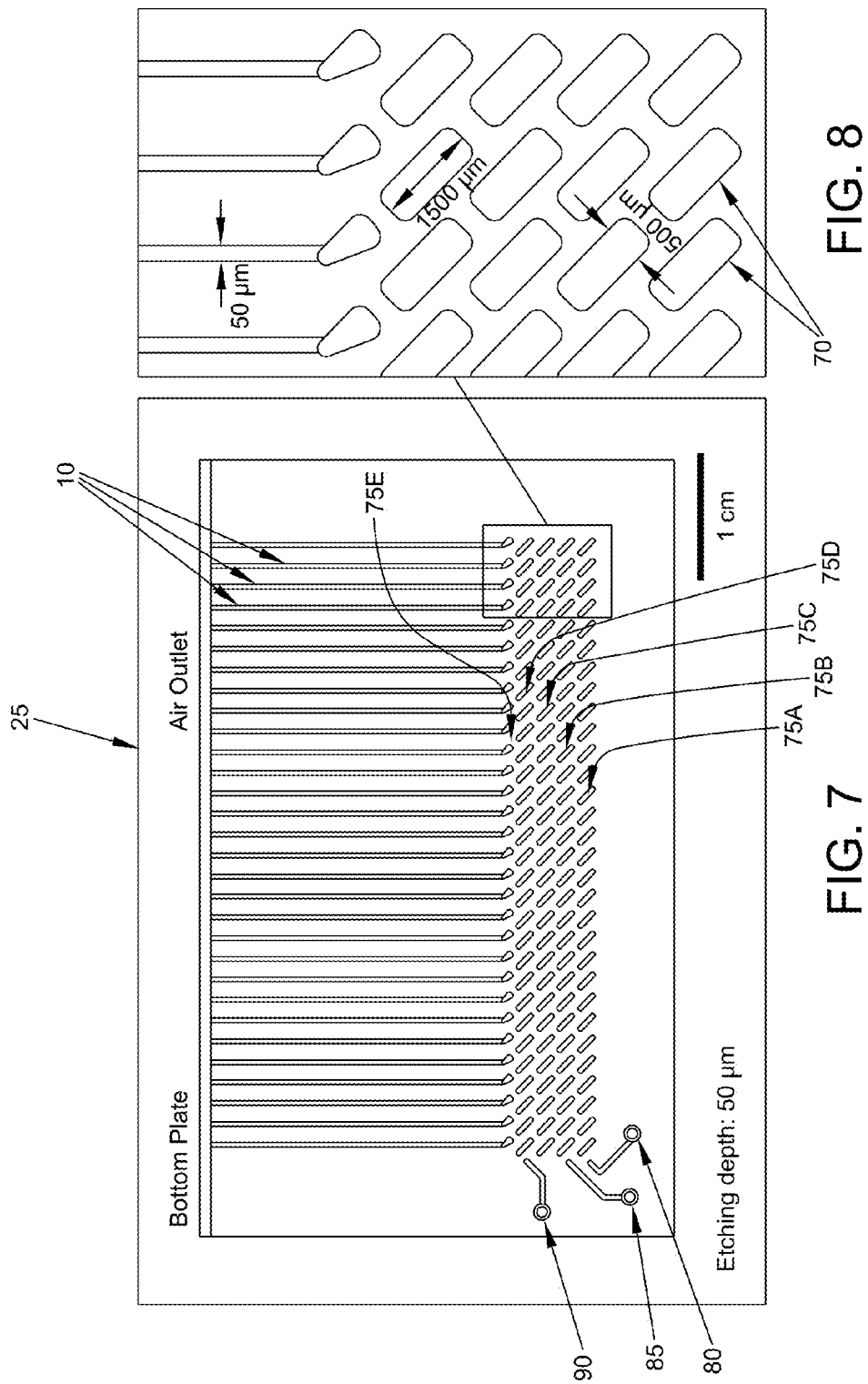

As seen in FIG. 3, the multi-protein measurements presented in bar chart form by multiplexed volumetric bar chart chip 5 may then be read with a smart-phone or barcode scanner 15, whereby to automate the data collection process.

Looking now at FIGS. 4-8, multiplexed volumetric bar chart chip 5 comprises two plates, a transparent top plate 20 and a bottom plate 25 (which may or may not be transparent).

Top plate 20 (FIGS. 5 and 6) has a plurality of recesses 30 formed on its bottom surface, with recesses 30 being arranged in a plurality of rows 35 (i.e., 35A, 35B, 35C, etc.), with each of the recesses 30 extending at a 45 degree angle relative to the axis of a given row 35, and with a recess 30 in one row 35 being aligned with an offset recess 30 in an adjacent row 35. An inlet 40 is connected to a far side recess 30 on the ultimate row 35A, and an outlet 45 is formed adjacent to the opposite far side recess 30 on the same ultimate row 35A. An inlet 50 is connected to a far side recess 30 on the penultimate row 35B, and an outlet 55 is formed adjacent to the opposite far side recess 30 on the same penultimate row 35B. The antepenultimate row 35C lacks both an inlet and an outlet. An inlet 60 is connected to a far side recess 30 on the ante-antepenultimate row 35D, and an outlet 65 is formed adjacent to the opposite far side recess 30 on the same ante-antepenultimate row 35D.

Figure 9:
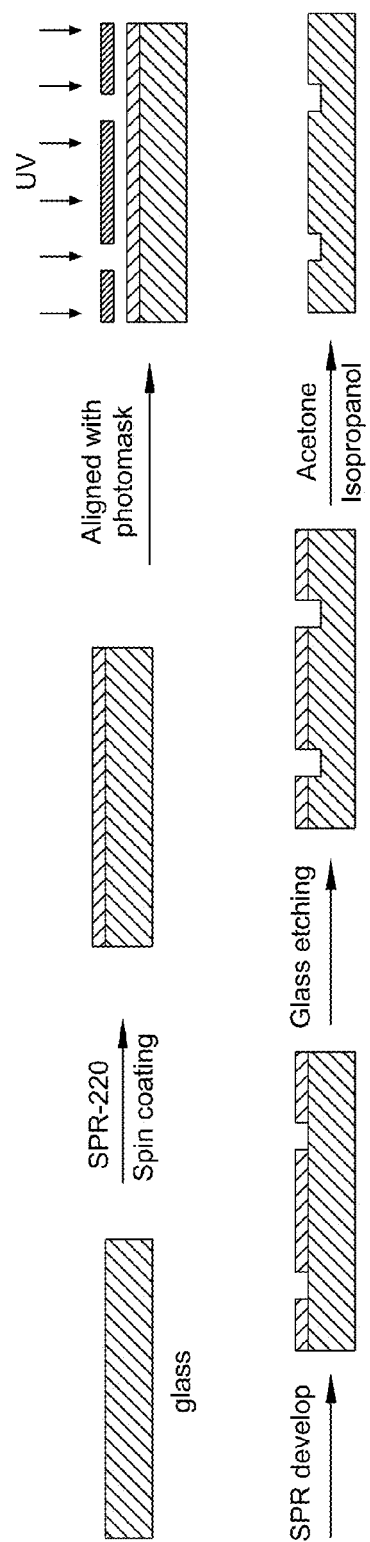
FIG. 9 is a schematic drawing of an etching process which can be utilized to form recesses and channels in the top plate and the bottom plate of multiplexed volumetric bar chart chip.

In one preferred form of the invention, and looking now at FIG. 9, recesses 30, inlets 40, 50, 60, and outlets 45, 55, 65 are all formed in the bottom surface of top plate 20 using a conventional etching process of the sort well known in the etching arts. Preferably, recesses 30, inlets 40, 50, 60 and outlets 45, 55, 65 are etched in the bottom surface of a glass plate. Alternatively, recesses 30, inlets 40, 50, 60 and outlets 45, 55, 65 may be formed in a silicon plate, a plastic plate, a ceramic plate, a quartz plate, a metal oxide plate or other appropriate substrate material.

Bottom plate 25 has a plurality of recesses 70 formed on its top surface, with recesses 70 being arranged in a plurality of rows 75 (i.e., 75A, 75B, 75C, etc.), with each of the recesses 70 extending at a 45 degree angle relative to the axis of a given row 75, and with a recess 70 in one row 75 being aligned with an offset recess 70 in an adjacent row 75. An outlet 80 is connected to a far side recess 70 on the ultimate row 75A. An outlet 85 is connected to a far side recess 70 on the penultimate row 75B. The antepenultimate row 75C lacks an outlet. An outlet 90 is connected to a far side recess 70 on the ante-antepenultimate row 75D. In addition, the plurality of bar channels 10 are formed on the top surface of bottom plate 25, with each of the bar channels 10 being connected to a recess 70 in the ante-ante-antepenultimate row 75E (see FIG. 8), and with each of the bar channels 10 extending parallel to one another and perpendicular to the axis of rows 75.

In one preferred form of the invention, and looking now at FIG. 9, recesses 70, outlets 80, 85, 90, and bar channels 10 are all formed in the top surface of bottom plate 25 using a conventional etching process of the sort well known in the etching arts. Preferably, recesses 70, outlets 80, 85, 90, and bar channels 10 are etched in the top surface of a glass plate. Alternatively, recesses 70, outlets 80, 85, 90, and bar channels 10 may be formed in a silicon plate, a plastic plate, a ceramic plate, a quartz plate, a metal oxide plate or other appropriate substrate material.

Figure 10:
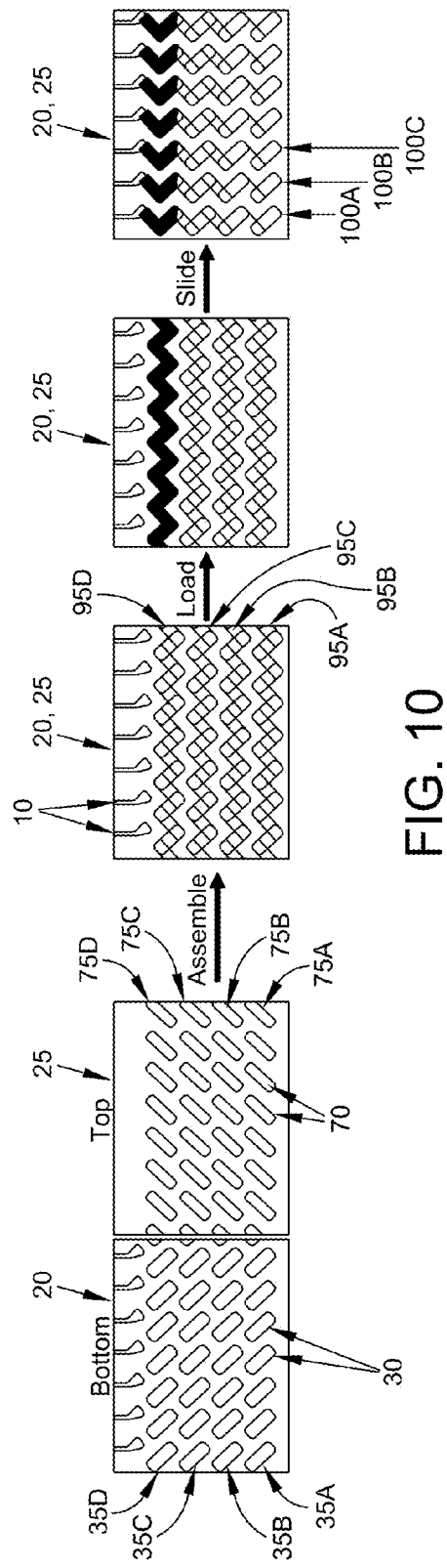
FIG. 10 is a schematic drawing of the assembly and operation of the multiplexed volumetric bar chart chip of the present invention.

Looking next at FIG. 10, top plate 20 is assembled on top of bottom plate 25 so that recesses 30 in top plate 20 communicate with recesses 70 in bottom plate 25. More particularly, when top plate 20 is assembled on top of bottom plate 25 in this manner, recesses 30 in top plate 20 will cooperate with recesses 70 in bottom plate 25 so as to initially form a plurality of continuous rows 95 (i.e., 95A, 95B, 95C, 95D, etc.) in multiplexed volumetric bar chart chip 5, with the inlet 40 of ultimate row 95A being connected with the outlet 45 of ultimate row 95A, with the inlet 50 of the penultimate row 95B being connected with the outlet 55 of the penultimate row 95B, and with the inlet 60 of the ante-antepenultimate row 95D being connected with the outlet 65 of the ante-antepenultimate row 95D. As noted above, the antepenultimate row 95C lacks both an inlet and an outlet.

Still looking now at FIG. 10, it will be appreciated that, due to the dispositions of recesses 30 in top plate 20 and recesses 70 in bottom plate 25, an oblique slide of top plate 20 relative to bottom plate 25 disrupts the aforementioned rows 95 and causes them to transform into a plurality of continuous columns 100 (i.e., 100A, 100B, 100C, etc.), with each column 100 being in fluid communication with one of the aforementioned bar columns 10.

In view of the foregoing construction, multiplexed volumetric bar chart chip 5 can be used to simultaneously determine the quantity of multiple proteins present in a sample, with the quantity of each specific protein being indicated in a particular one of the plurality of bar channels 10.

More particularly, and referring now to FIGS. 11 and 12, and as will hereinafter be discussed in further detail below, during manufacture of multiplexed volumetric bar chart chip 5, a different protein-specific antibody is bonded in a recess 30 of the penultimate row 35B. As a result, after the bottom plate 20 and top plate 25 are assembled together, row 75B will contain a series of different protein-specific antibodies, with a different protein-specific antibody being located in each recess 30 of the row 75B.

Prior to use, hydrogen peroxide ($H_2O_2$) is introduced into inlet 40 of multiplexed volumetric bar chart chip 5, whereby to fill the ultimate row 75A of multiplexed volumetric bar chart chip 5 with hydrogen peroxide. Red ink (or some other colored material which is readily discernible through top plate 25 and against bottom plate 20) is introduced into inlet 60 of multiplexed volumetric bar chart chip 5, whereby to fill the ante-antepenultimate row 75D of multiplexed volumetric bar chart chip 5 with red ink. Antepenultimate row 75C is intentionally left blank to serve as an air spacer, thereby avoiding direct contact between a sample and the red ink.

Then, when a sample is to be checked for the presence and quantity of specific proteins (i.e., the proteins which will bind to the protein-specific antibodies already bound to the recesses 30 of row 75B), the sample is introduced into inlet 50 of multiplexed volumetric bar chart chip 5 so that the sample fills the penultimate row 75B. This action causes the sample to mix with the different protein-specific antibodies which are bonded to bottom plate 20 in the recesses 30, so that the target proteins bind to the appropriate protein-specific antibodies in the recesses 30. Significantly, each target protein binds to only one protein-specific antibody, and such binding takes place in only one of the recesses 30 in the penultimate row 75B. Thereafter, the penultimate row 75B is flushed so as to remove any materials which are not bound to a protein-specific antibody.

Next, catalase is introduced into inlet 50 of multiplexed volumetric bar chart chip 5 so as to fill the penultimate row 75B. This action causes the catalase to bind to the target proteins which are themselves bound to the protein-specific antibodies in the recesses 30. It will be appreciated that, to this end, the catalase is a mixture of all the catalase detecting probes required for binding to the target proteins (e.g., silica nanoparticles conjugated with detecting antibodies and catalase molecules). Then excess catalase is rinsed from the penultimate row 75B.

Thereafter, top plate 25 is slid obliquely relative to bottom plate 20, causing rows 75 (i.e., 75A, 75B, 75C, 75D, etc.) to be disrupted and transformed into columns 100 (i.e., 100A, 100B, 100C, etc.). As this row-to-column transformation occurs, each recess 30 (containing the protein-specific antibodies and any target proteins bound thereto and any catalase bound thereto) previously located in penultimate row 75B becomes incorporated as a section of a specific column 100 (i.e., 100A, 100B, 100C, etc.). In addition, as this row-to-column transformation occurs, the hydrogen peroxide contained in row 75A is permitted to advance up each of the columns 100 and thereby mix with any catalase bound to the target proteins (which are themselves bound to the protein-specific antibodies), the mixing of which causes a reaction which releases oxygen gas. The oxygen gas is produced in proportion to the quantity of catalase present in a given column (and hence in proportion to the quantity of target proteins which are present in a given column). Thus, the quantity of oxygen gas produced in a given column 100 is proportional to the quantity of target proteins which are present in a given column 100, with each of the columns 100 containing a different target protein (by virtue of the fact that each of the columns 100 contains a different protein-specific antibody). The oxygen gas produced by the reaction accumulates within the limited volume of columns 100 and causes an increase in pressure, which propels the red ink contained in columns 100 into and along bar columns 10, with the ink advancing a distance along bar columns 10 which is proportional to the quantity of oxygen gas produced in that column, which is in turn proportional to the quantity of the target proteins which are bound to the protein-specific antibodies disposed in the recesses associated with that column.

Figure 13:
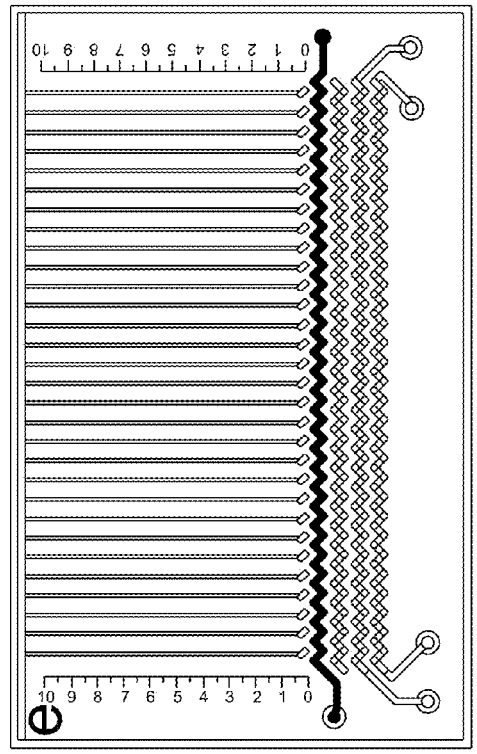
FIG. 13 shows the multiplexed volumetric bar chart chip of the present invention prior to the oblique sliding of the top plate relative to the bottom plate.
Figure 14:
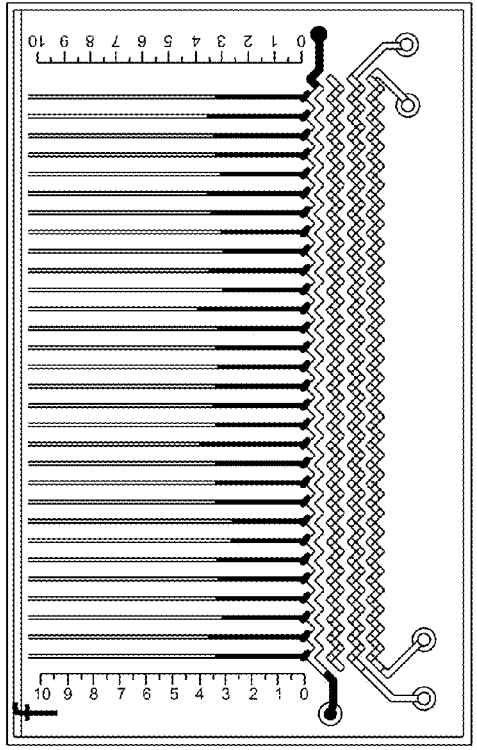
FIGS. 14-16 show the test results obtained in accordance with the present invention for various samples.
Figure 15:
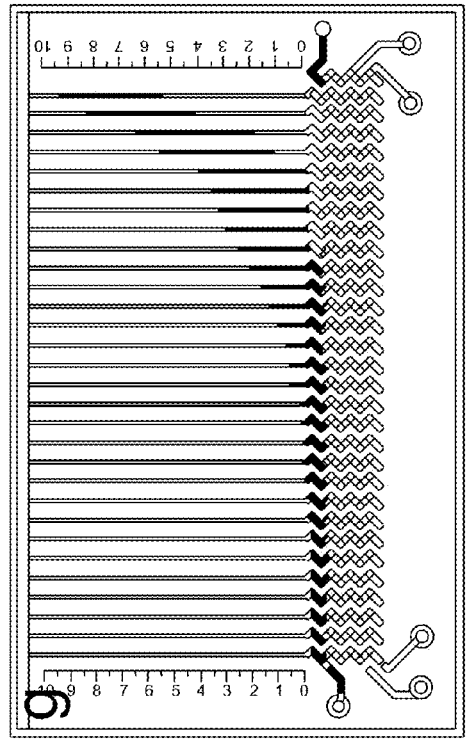
Figure 16:
Figure 21:
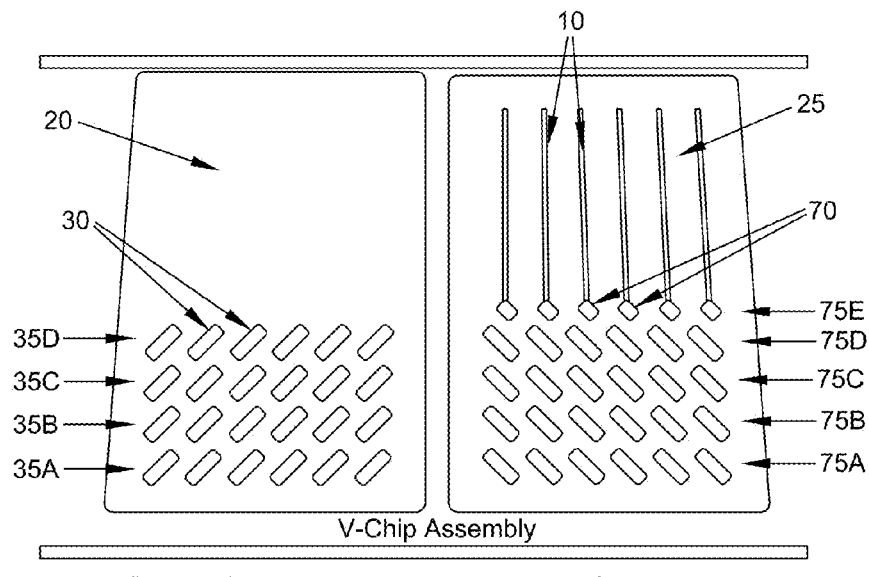
FIGS. 21-32 are a schematic series of views illustrating the assembly and operation of the multiplexed volumetric bar chart chip in one form of the present invention.
Figure 22:
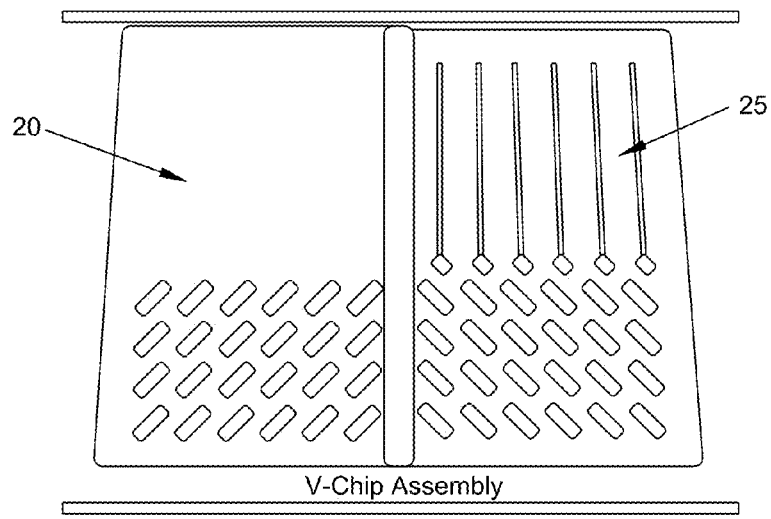
Figure 23:
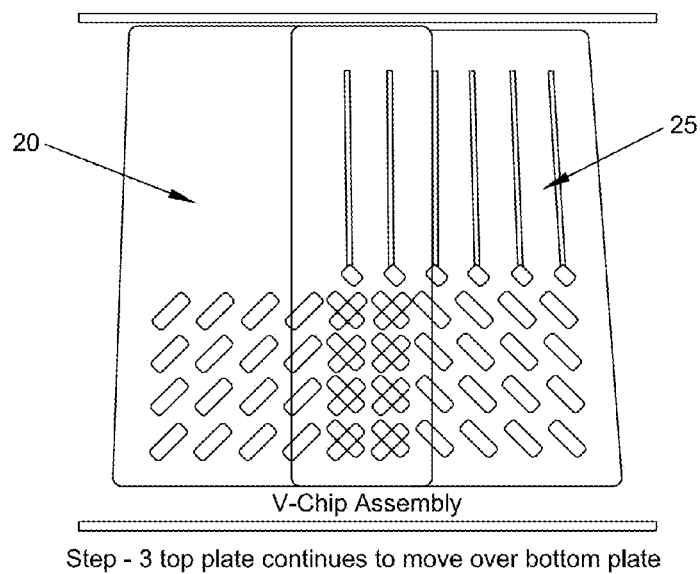
Figure 24:
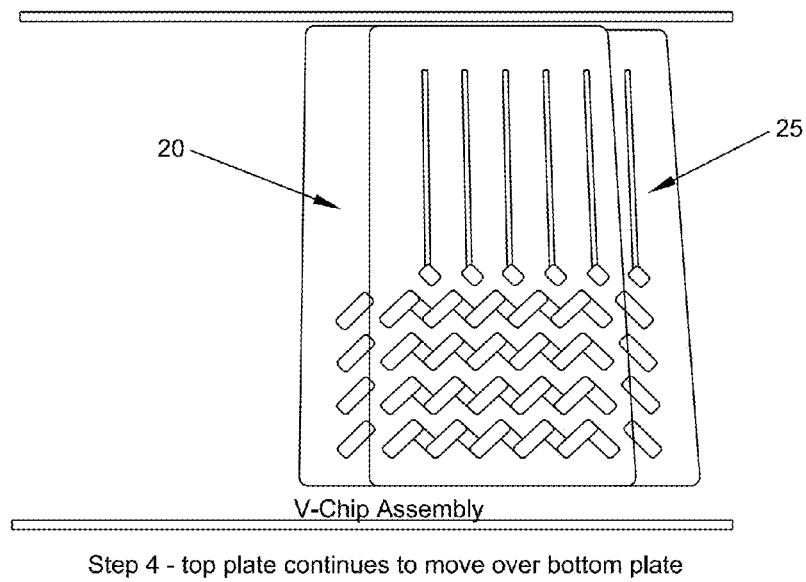
Figure 25:
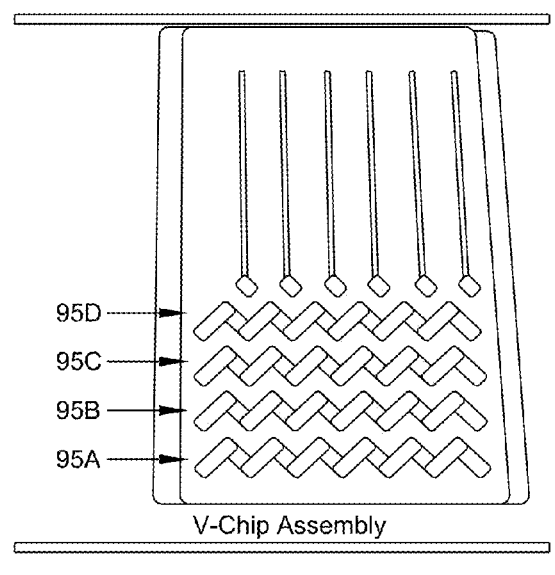
Figure 26:
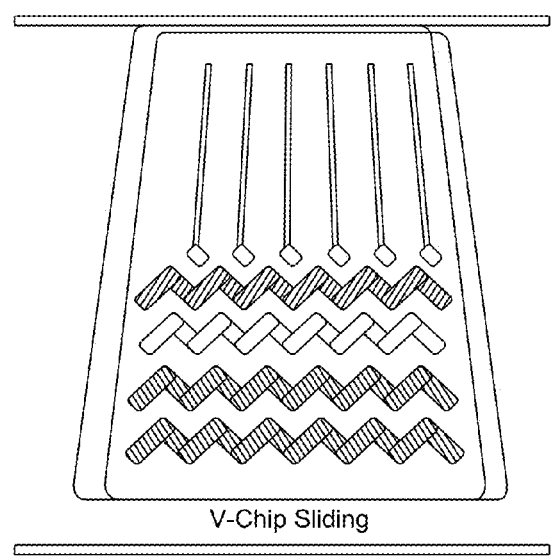
Figure 27:
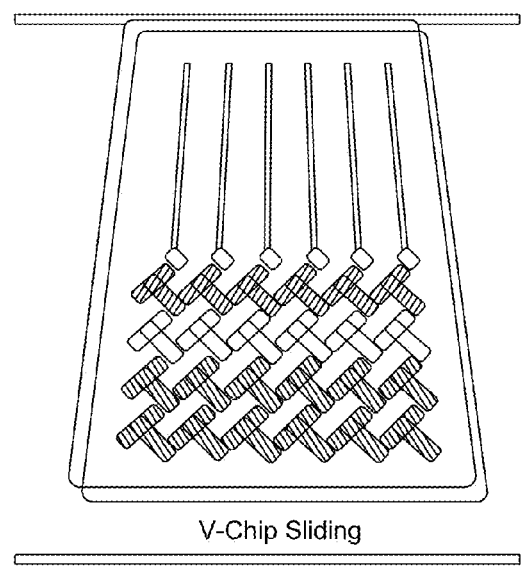
Figure 28:
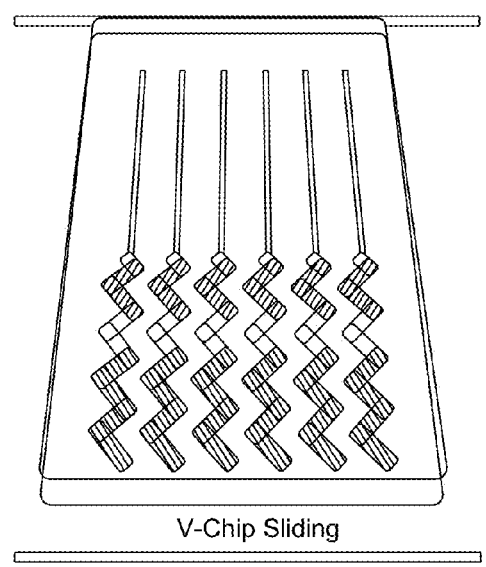
Figure 29:
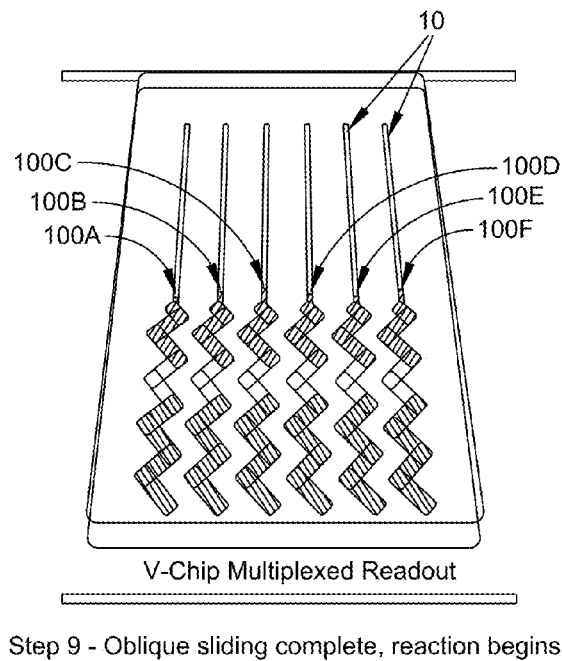
Figure 30:
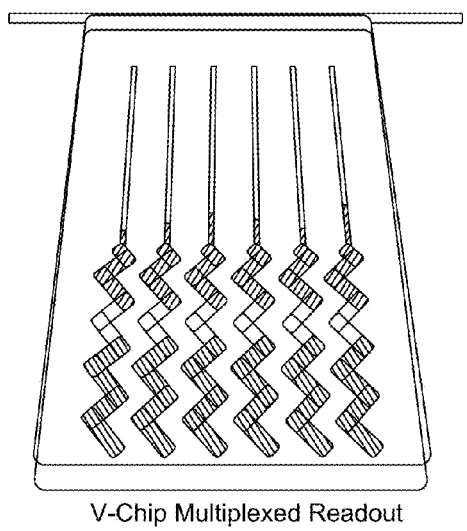
Figure 31:
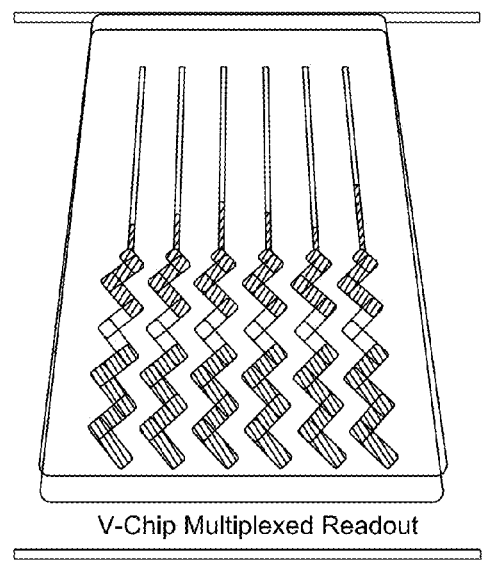
Figure 32:
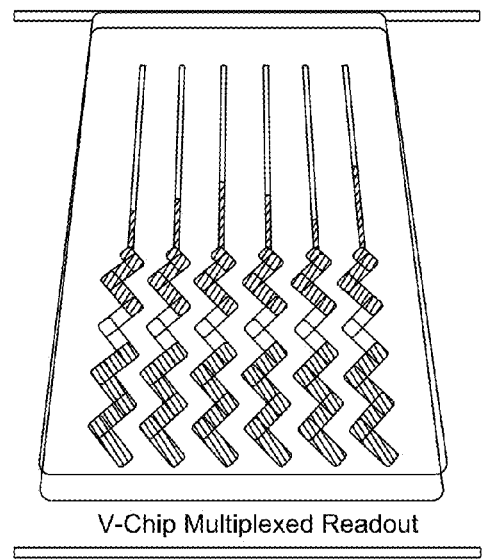
Figure 33:
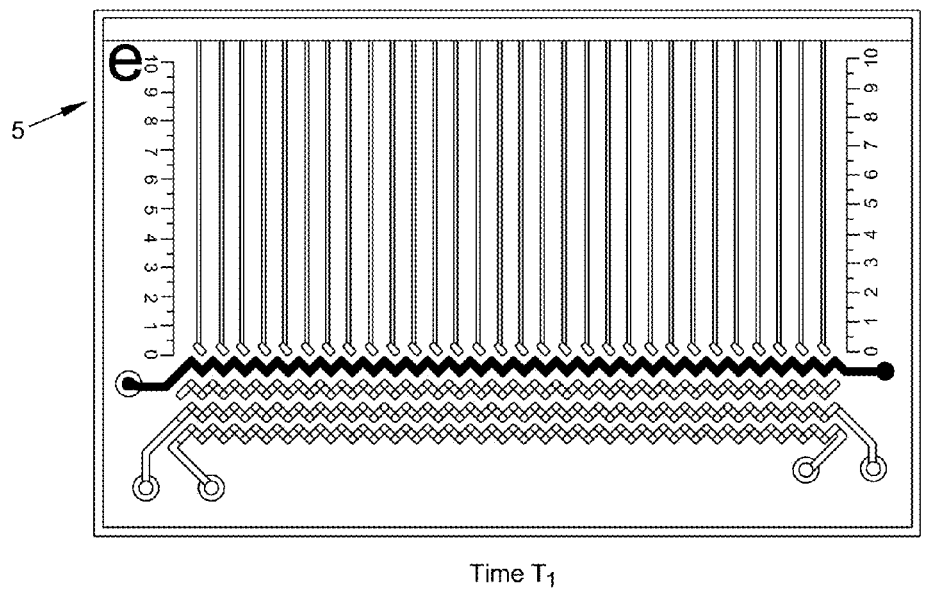
FIGS. 33-45 are a schematic series of views showing how, over time, the ink in various bar channels advance in the multiplexed volumetric bar chart chip according to the quantity of target proteins or other types of biomarkers or other molecular analytes present in the sample.
Figure 34:
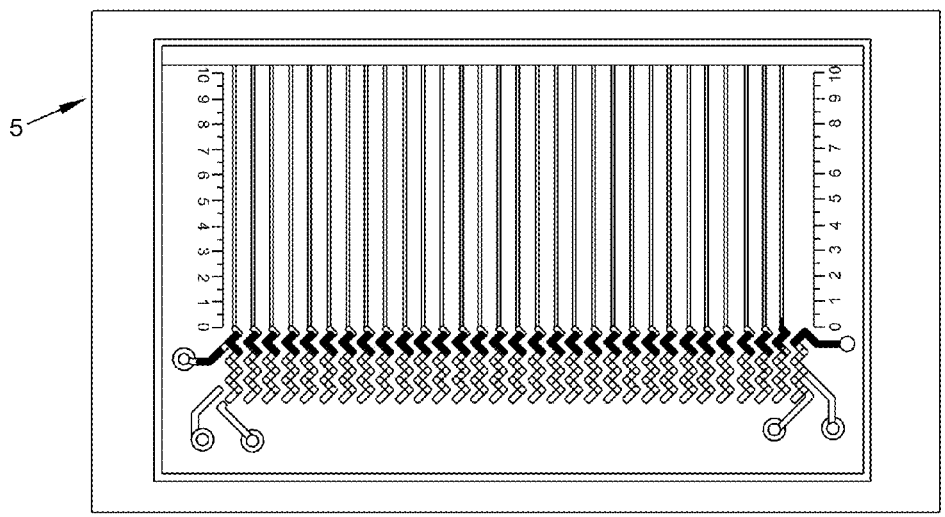
Figure 35:
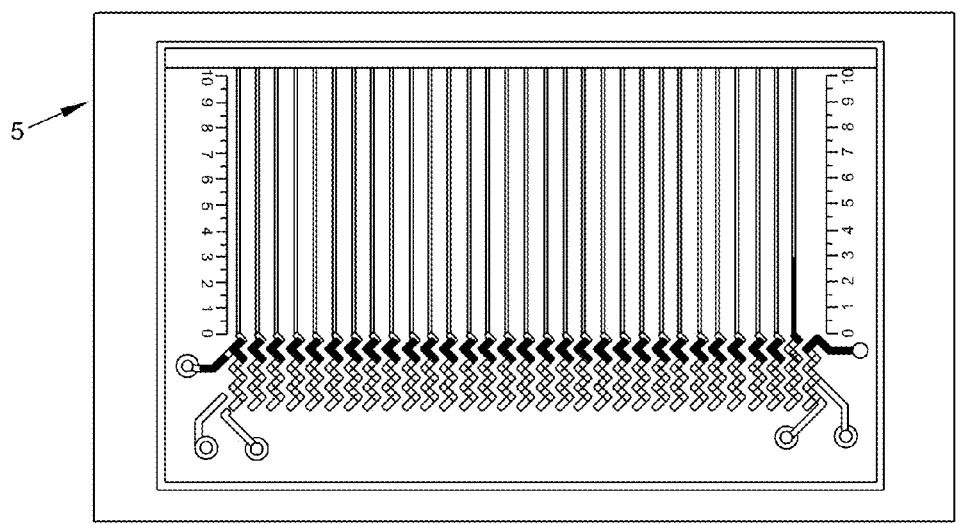
Figure 36:
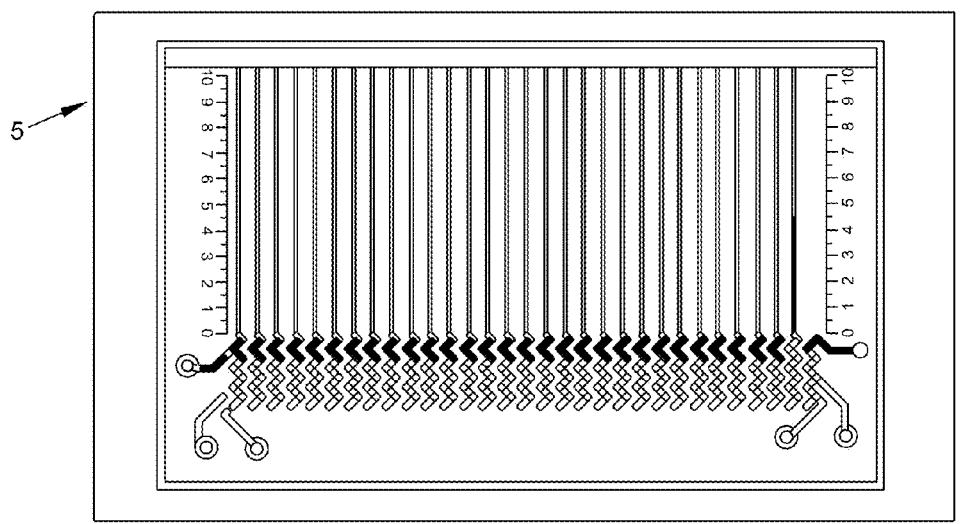
Figure 37:
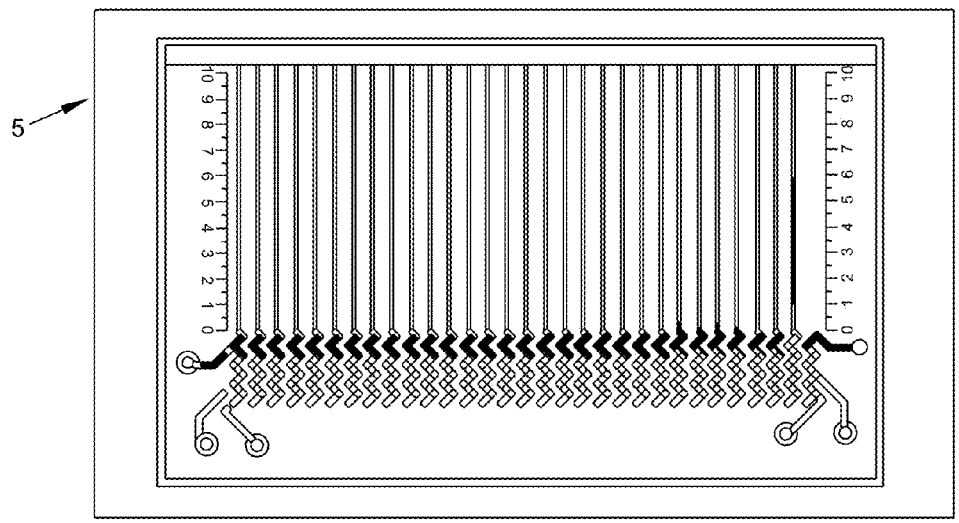
Figure 38:
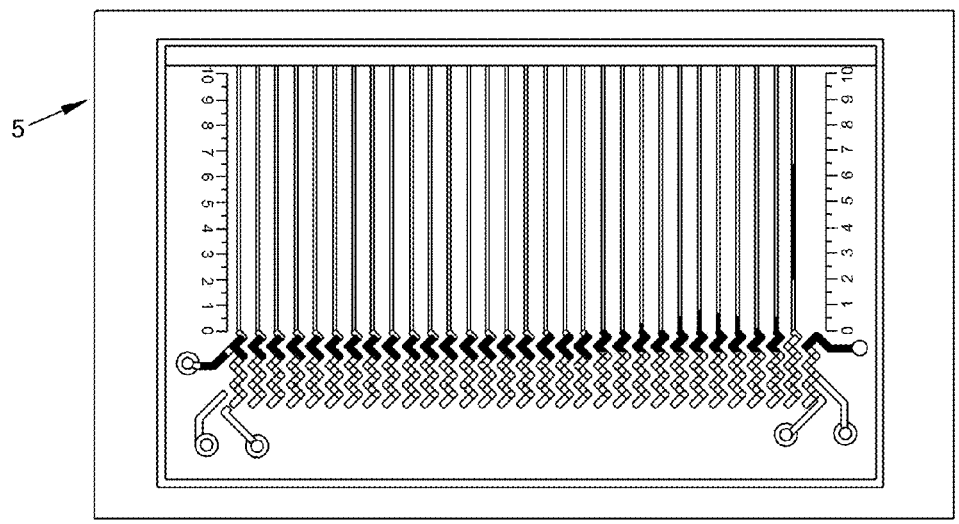
Figure 39:
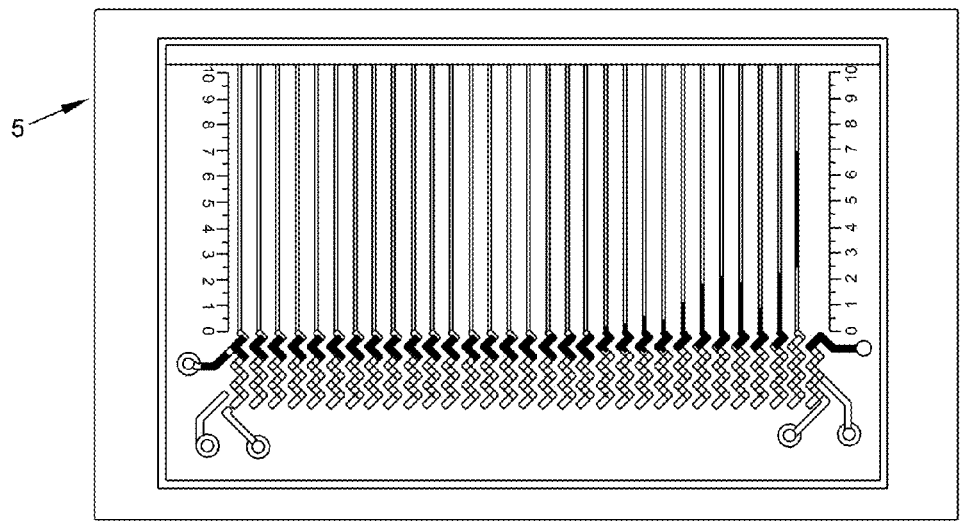
Figure 40:
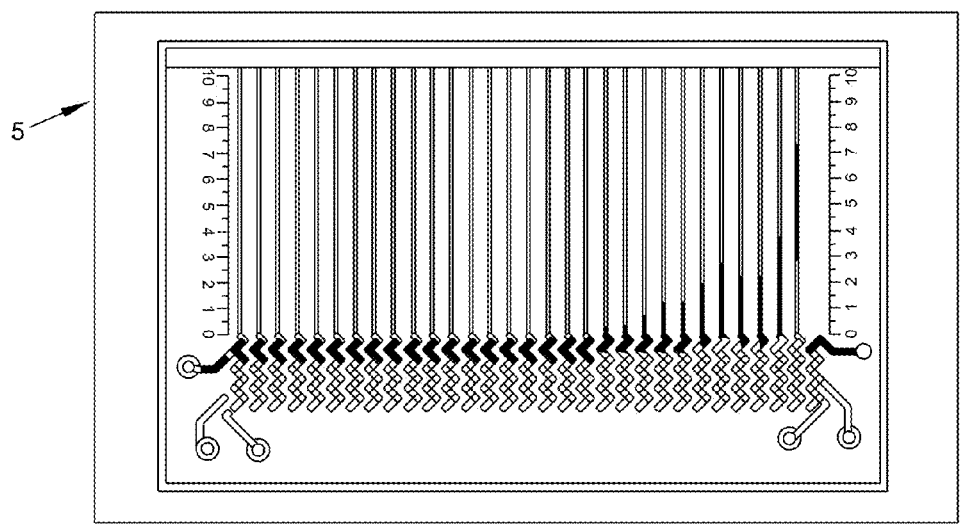
Figure 41:
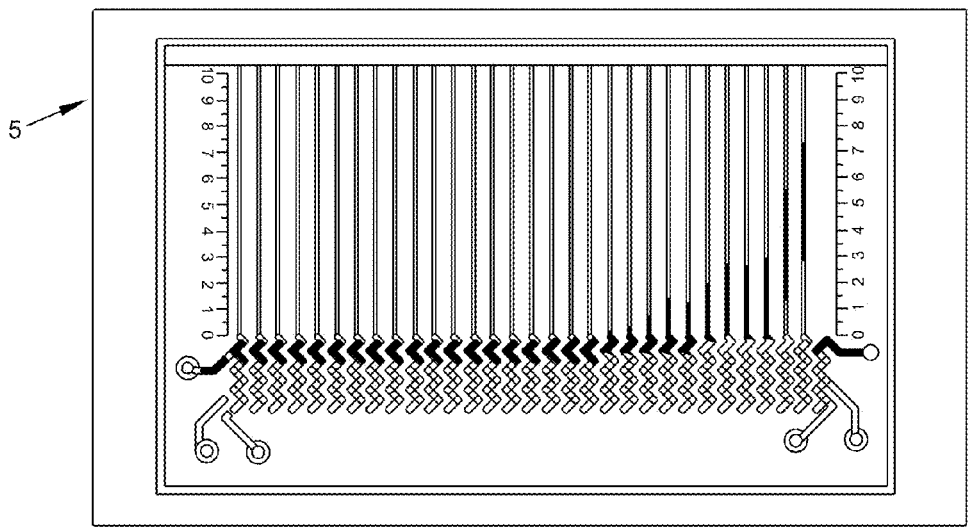
Figure 42:
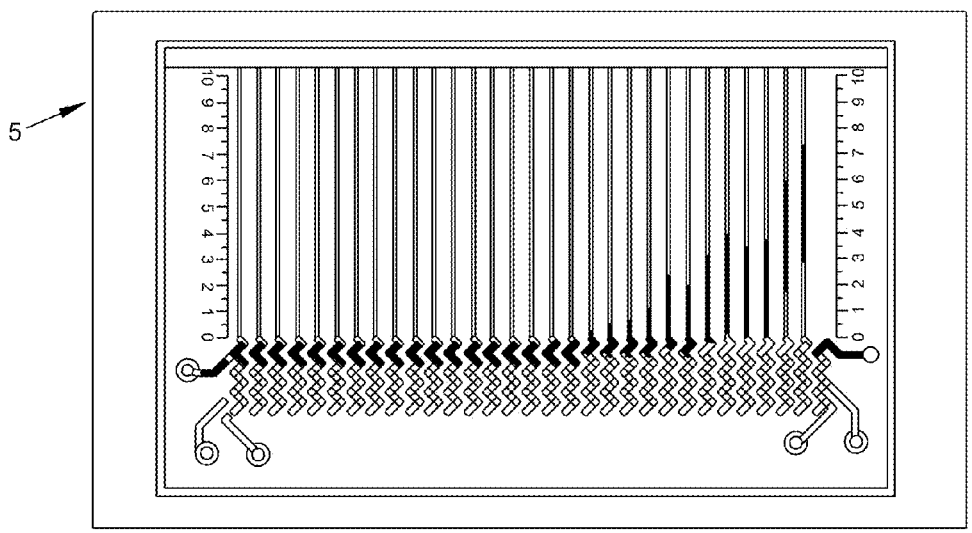
Figure 43:
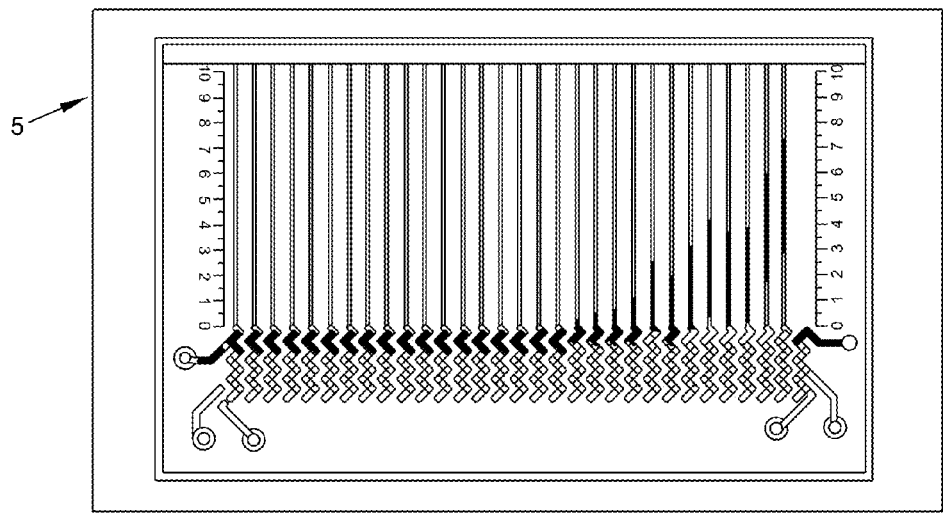
Figure 44:
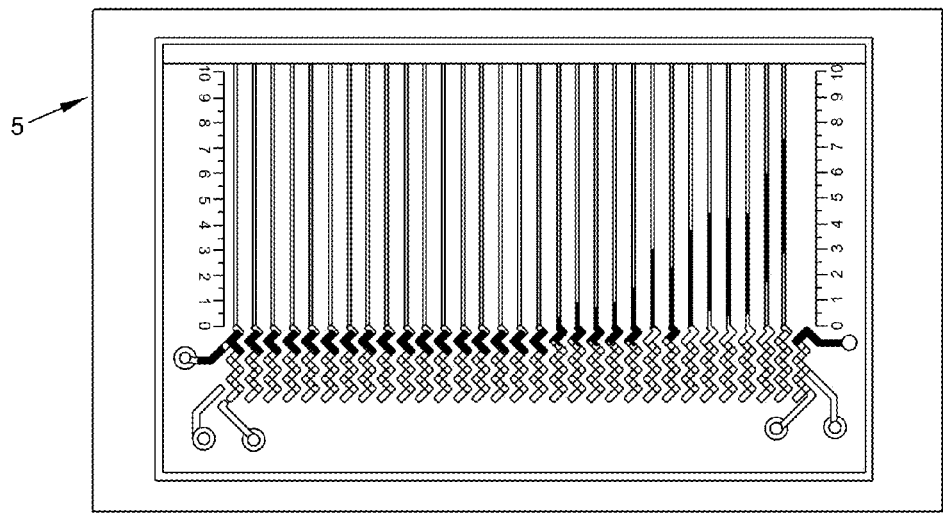
Figure 45:
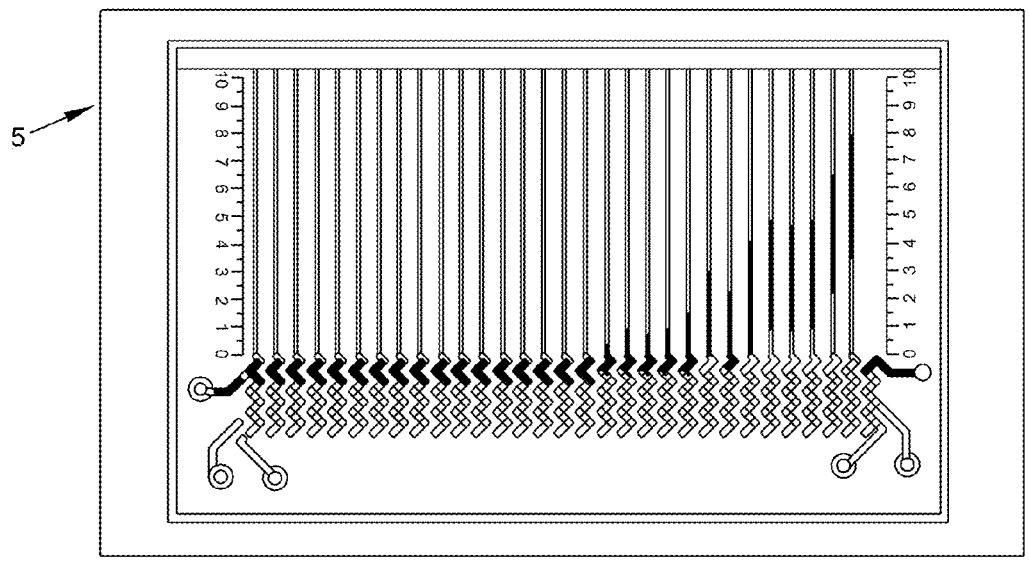

As a result of the foregoing, by disposing different protein-specific antibodies in different ones of the recesses 30 of rows 35 of bottom plate 20, multiplexed volumetric bar chart chip 5 can be used to simultaneously determine the quantity of multiple proteins present in a sample, with the quantity of each protein being indicated in a particular one of a plurality of bar channels 10. See, for example, FIGS. 13-16, where FIG. 13 shows multiplexed volumetric bar chart chip 5 prior to the oblique sliding of top plate 25 relative to bottom plate 20, and FIGS. 14-16 show the test results for various samples.

FIGS. 17-20 show specific steps in the foregoing process. Specifically, FIG. 17 shows a protein-specific antibody being bound in a recess 30 of bottom plate 20; FIG. 18 shows a sample being loaded into a recess 30 of bottom plate 20, whereby to bind a target protein to a protein-specific antibody; FIG. 19 shows catalase being loaded into a recess 30 so as to bind catalase to a target protein (which is itself bound to a protein-specific antibody); and FIG. 20 shows hydrogen peroxide being loaded into a recess 30, whereby to release oxygen gas in proportion to the quantity of target protein present in a recess 30.

If desired, the same protein-specific antibody can be bound in multiple recesses 30 of penultimate row 35B of bottom plate 20, whereby to provide redundancy.

FIGS. 21-32 are a schematic series of views showing the assembly and operation of the multiplexed volumetric bar chart chip in one preferred form of the present invention.

FIGS. 33-45 are a schematic series of views showing how, over time, the ink in a given bar channel advances a distance along that bar channel which is proportional to the quantity of the target protein which are bound to the protein-specific antibody disposed in the recess associated with that bar channel, whereby to indicate, in multiplexed volumetric bar chart form, the results of a simultaneous multi-protein assay.

The novel method and apparatus of the present invention provides instant and visual quantitation of target biomarkers or other molecular analytes and provides a visualized bar chart without the use of instruments, data processing or graphic plotting. Thus, since the novel method and apparatus of the present invention does not require the use of complex instruments, the novel method and apparatus of the present invention can be easily used as a point of care determination of the quantity of a protein (and, preferably, the quantity of multiple proteins) present in a sample. More particularly, the novel method and apparatus of the present invention can be used as a point of care determination of the quantity of protein, nucleic acid, peptide, sugar, organic compounds, polymer, metal ions, and other molecular analytes, as well as the quantity of bacteria, cells, and particles.

In the foregoing description, gas is generated by the reaction of an ELISA probe with a reagent, and specifically, gas is generated by the reaction of the ELISA probe (i.e., the protein-specific antibody which is bound to the target protein which is bound to the catalase) with hydrogen peroxide. It is important to note that many other combinations of a probe and a reagent may be used to generate gas. By way of example but not limitation, such probe and reagent combination may include catalase and hydrogen peroxide, platinum film or particles and hydrogen peroxide, catalase and carbamide peroxide, zinc and chloric acid, iron and chloric acid, and other similar combinations. Thus, since the multiplexed volumetric bar chart chip readout is based on the volumetric measurement of a gas generation, many fast responsive gas generation schemes can be used for the system, including catalase with hydrogen peroxide, catalase and carbamide peroxide, zinc and chloric acid, iron and chloric acid, and other similar combinations.

Furthermore, the multiplexed volumetric bar chart chip is based on a sandwich assay. In the foregoing description, a capture antibody binds to an analyte and a detecting antibody conjugated with a catalase probe indicates the amount. Thus, the sandwich scheme is made up of capture antibody/analyte/detecting antibody conjugated with a catalase probe.

Figure 46:
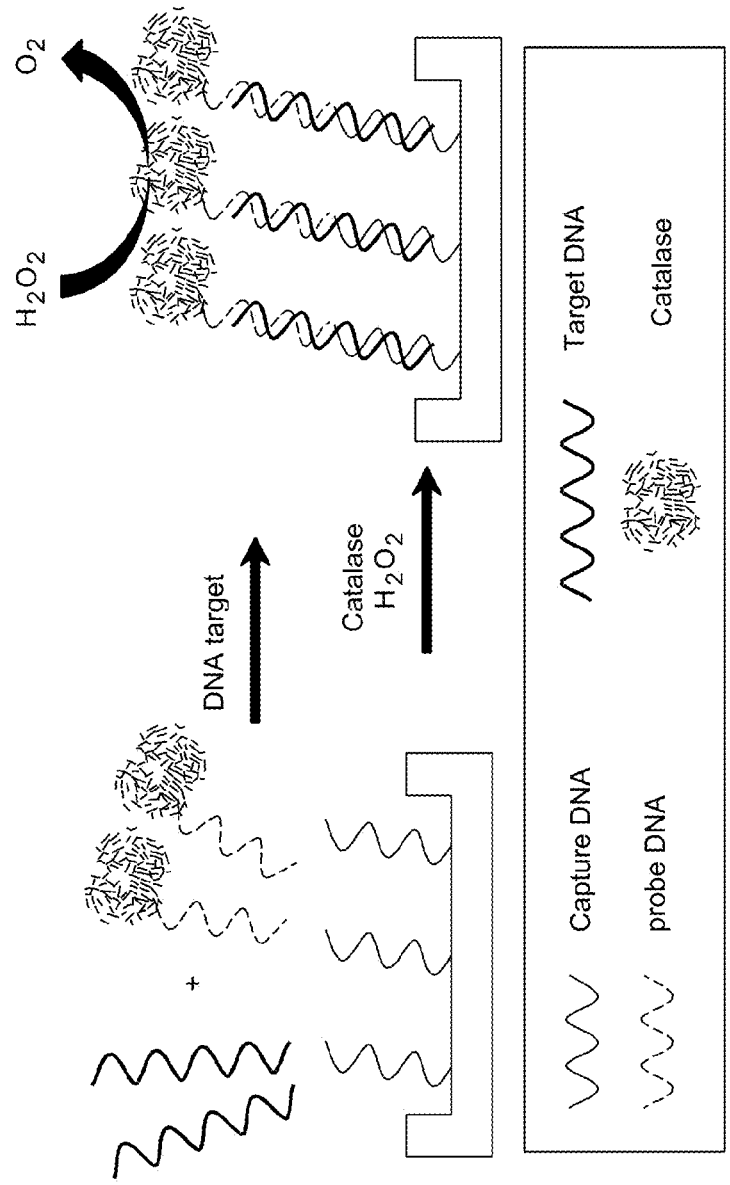
FIG. 46 illustrates specific steps which are performed in accordance with a DNA assay scheme and oxygen generation mechanism.

This type of sandwich scheme could also be extended to nucleic acid hybridization, where the sandwich is capture DNA strand/target strand/detecting DNA strand (i.e., the target strand has a first half complimentary to the capture DNA strand and a second half complimentary to the detecting DNA strand). By way of example but not limitation, see FIG. 46, which shows specific steps that are performed in accordance with a DNA assay scheme and oxygen generation mechanism.

Additionally, this type of sandwich scheme could also be extended to hydrogen bonding, electrostatic reaction or interaction, or covalent bonding, where the target analyte is captured by a surface with a coating that can adhere the analyte by either hydrogen bonding, electrostatic reaction or interaction or the formation of a covalent bond. The readout of the adhered or bonded analyte can then be detected by the detecting antibody with a catalase probe. The sandwich of these types are surfaces (with adhesion forces of hydrogen bonding, electrostatic interaction or covalent bonding)/analyte/probe of detecting antibody with catalase.

Figure 47:
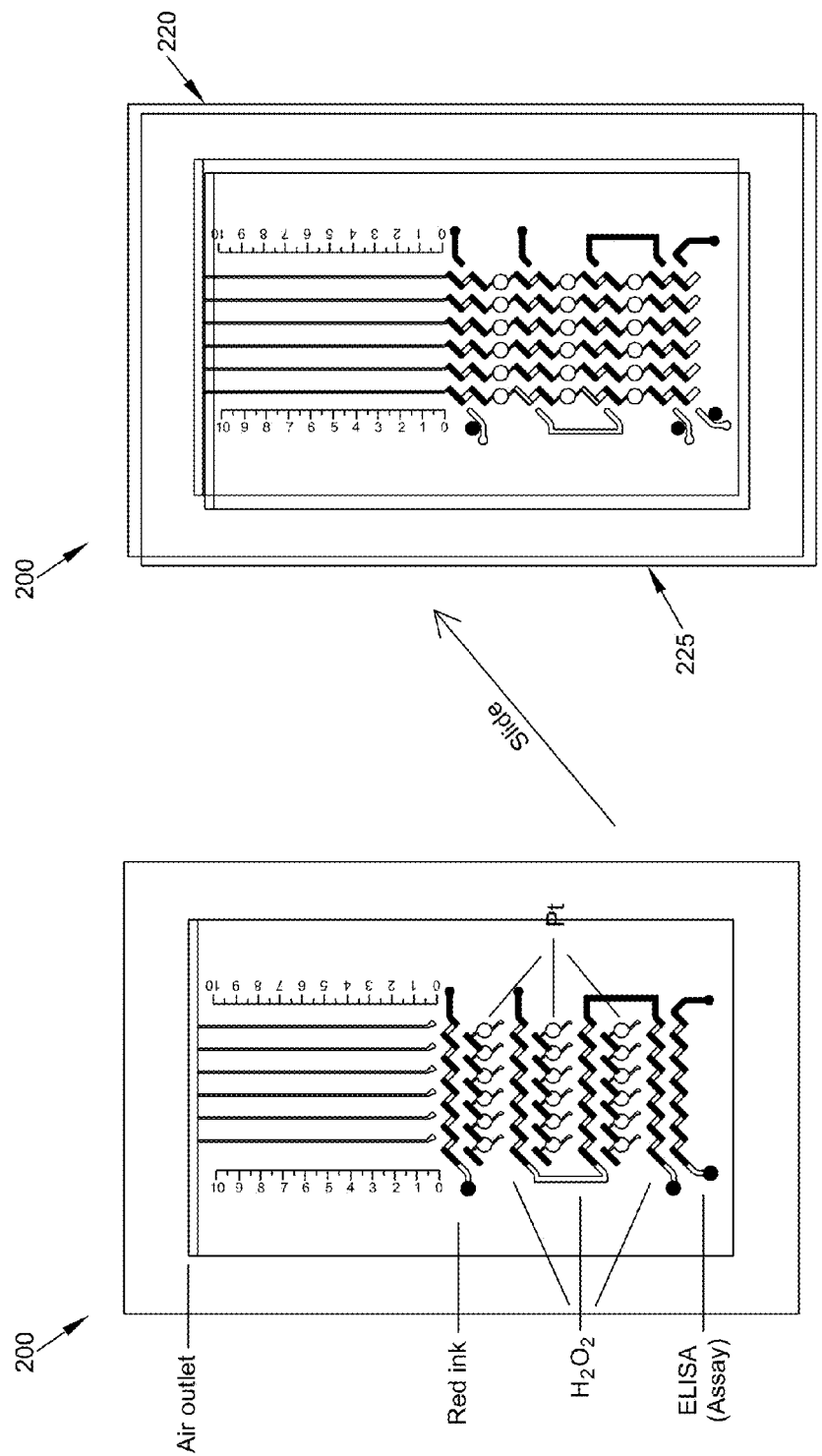
FIG. 47 shows an alternative embodiment of the novel multiplexed volumetric bar chart chip of the present invention.

In another embodiment of the present invention, and looking now at FIG. 47, a novel multiplexed volumetric bar chart chip 200 is provided which may be used in accordance with the present invention to determine the quantity of a target protein or other types of biomarkers or other analytes, wherein the signal for determining the quantity of the target protein or other types of biomarkers or other analytes is amplified.

More particularly, multiplexed volumetric bar chart chip 200 comprises two glass plates, a transparent top plate 220 and a bottom plate 225 (which may or may not be transparent).

Top plate 220 and bottom plate 225 are similar to top plate 20 and bottom plate 25 discussed above, except that the plurality of rows are arranged on the multiplexed volumetric bar chart chip 200 so that the recesses in the rows are filled with the ELISA reagents (Assay) (i.e., the protein-specific antibody, with the sample and catalase bound thereto), hydrogen peroxide, platinum film, hydrogen peroxide, platinum film, hydrogen peroxide, platinum film and ink.

Figure 48:
FIG. 48 shows images of hydrogen peroxide solution pushed into platinum wells using the multiplexed volumetric bar chart chip of FIG. 47.

As the ELISA reagent reacts with the hydrogen peroxide, oxygen is generated, with that oxygen being proportional to the quantity of the target antibody present in the sample. The oxygen generated by the ELISA reaction in turn drives a quantity of unreacted hydrogen peroxide (that is proportional to the quantity of oxygen produced from the ELISA reaction) into the next row of the chip (which contains platinum film). When this unreacted hydrogen peroxide passes into the row containing the platinum film, additional oxygen is generated, with the quantity of oxygen generated being proportional to (but greater than) the quantity of oxygen produced from the original ELISA reaction). This process cascades down the successive rows of the chip and, with each step, the amount of oxygen produced is proportional to (but successively greater than) the original quantity of oxygen produced by the ELISA reaction, which is in turn proportional to the quantity of the target protein or other types of biomarkers or other analytes present in the sample. However, since more oxygen is produced by each successive hydrogen peroxide/platinum film reaction, the signal (i.e., the advancement of the red ink in the plurality of channels) is amplified. Since the advancement of the red ink is the sum of the catalase reacting with hydrogen peroxide and the results of the platinum film reacting with hydrogen peroxide over three steps, multiplexed volumetric bar chart chip 200 exhibits a higher sensitivity than the multiplexed volumetric bar chart chip 5 discussed above. See, for example, FIG. 48, which shows images of hydrogen peroxide solution being pushed into successive platinum wells. Due to the accumulated volume of oxygen at different stages of the chip, more hydrogen peroxide was pushed into the platinum wells at the higher stage than at the lower stage.

Figure 49:
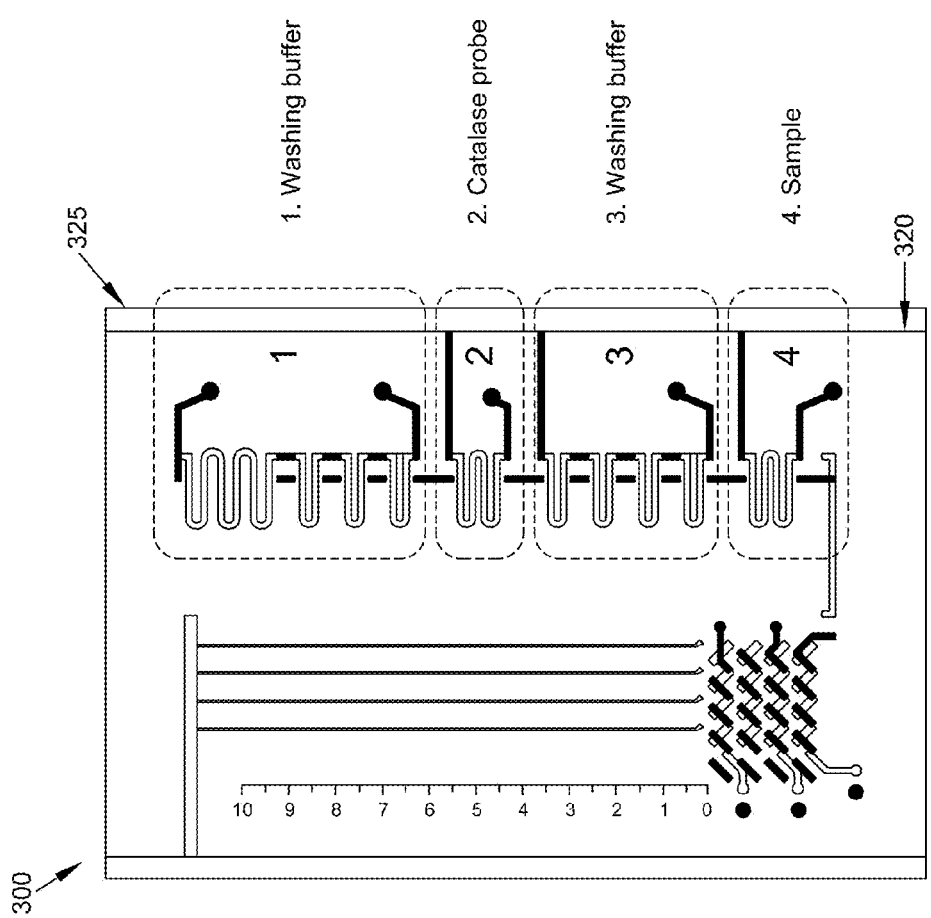
FIGS. 49 and 50 show an alternative embodiment of the novel multiplexed volumetric bar chart chip of the present invention.
Figure 50:
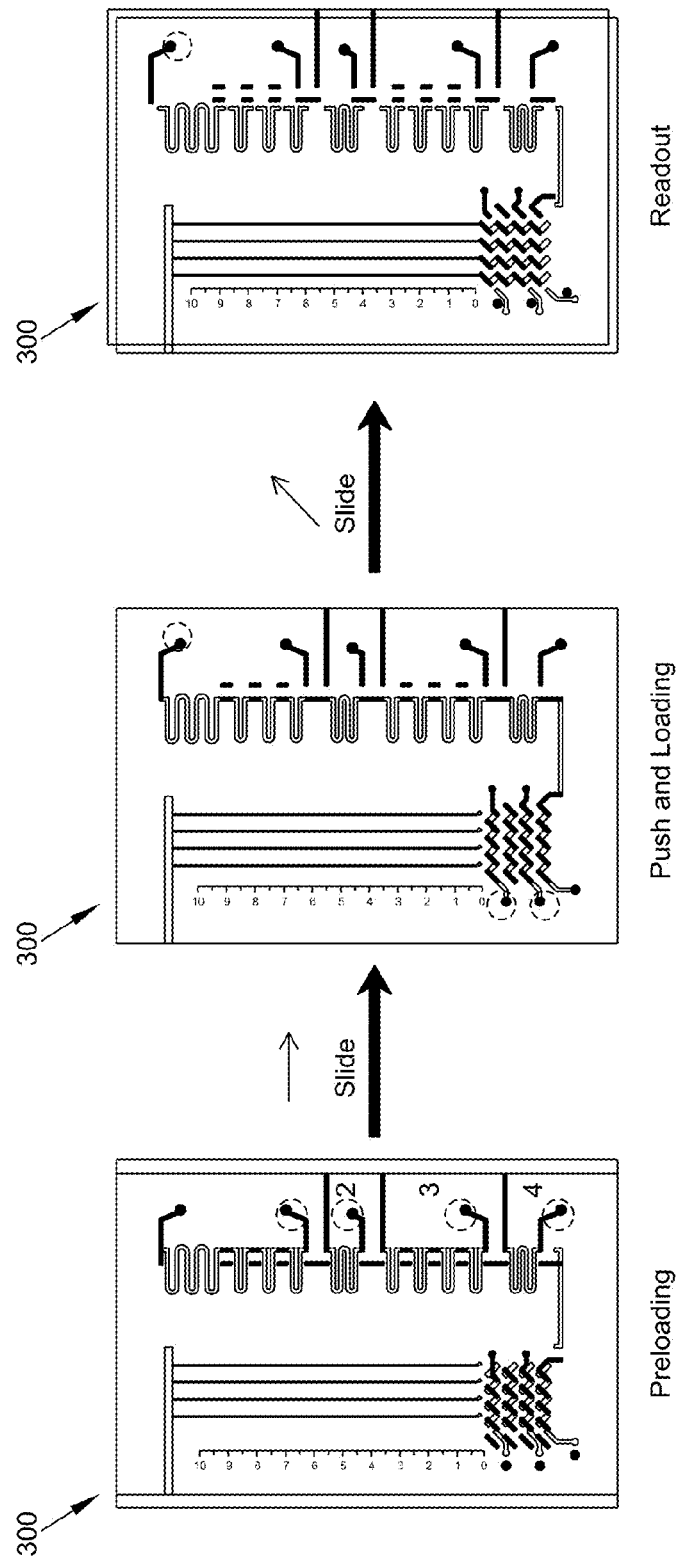

In still another embodiment of the present invention, and looking now at FIGS. 49 and 50, a novel multiplexed volumetric bar chart chip 300 is provided. Multiplexed volumetric bar chart chip 300 is similar to multiplexed volumetric bar chart chip 5 discussed above, except that multiplexed volumetric bar chart chip 300 is manufactured so as to reduce the reagent loading and washing steps required for a user.

In this embodiment, the ELISA reagents (i.e., the washing buffer, catalase probe and washing buffer) can be preloaded in the multiplexed volumetric bar chart chip during the manufacturing stage (e.g., at the locations shown in FIG. 49). At the time of use, the sample is positioned in the multiplexed volumetric bar chart chip (e.g., at the location shown in FIG. 49). Then, the multiplexed volumetric bar chart chip is slid vertically so that the sample, washing buffer, catalase probe and washing buffer are sequentially passed through the ELISA reagent row of the chip, whereby to prepare the ELISA row of the chip in a single action. Subsequently, the multiplexed volumetric bar chart chip can be slid in the oblique direction so as to activate the oxygen reaction and generate the desired results.

In this form of the invention, the user will only need to load the sample into the chip and then slide the chip obliquely so as to activate the assay process.

Figure 51:
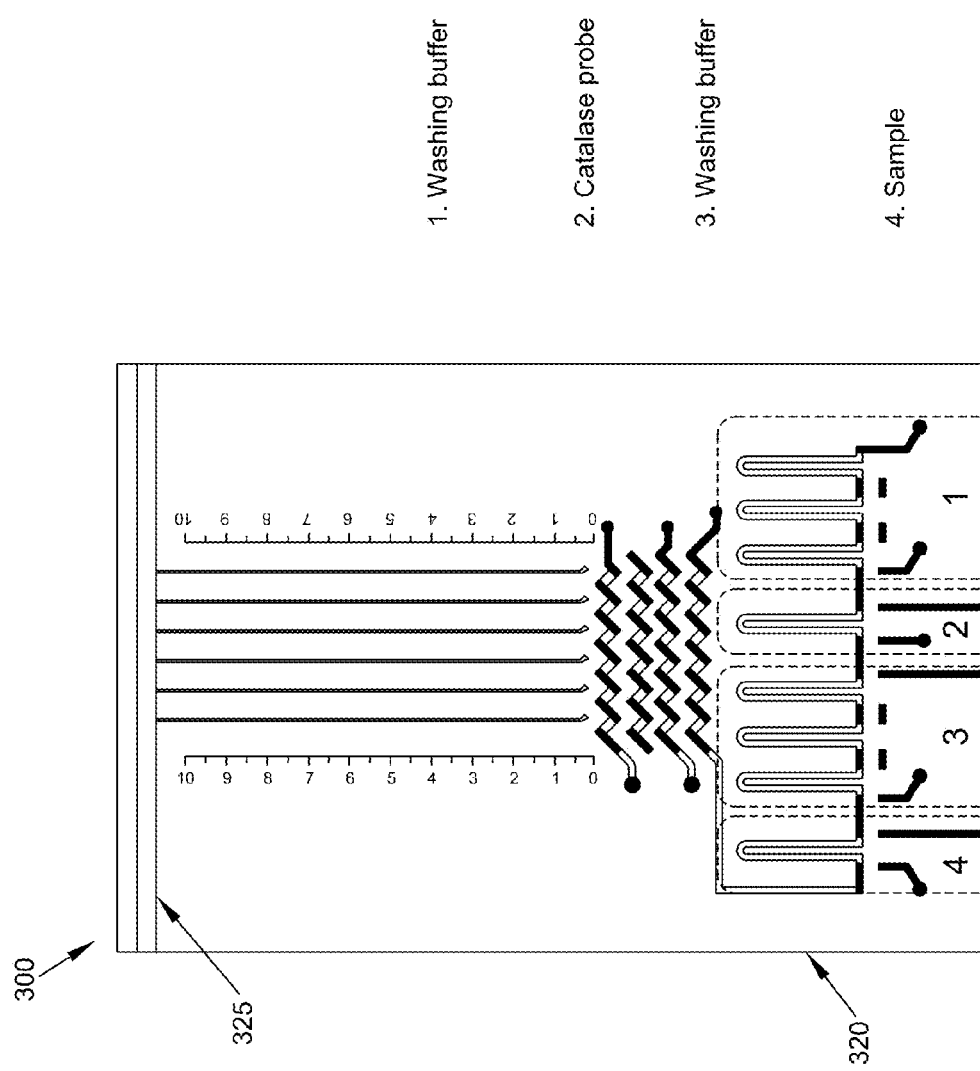
FIG. 51 shows an alternative embodiment of the novel multiplexed volumetric bar chart chip of the present invention.

FIG. 51 shows another form of the present invention in which the multiplexed volumetric bar chart chip is configured to load the ELISA row of the chip through a horizontal motion.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. Apparatus for determining the quantity of a target protein and other types of biomarkers or analytes present in a sample, the apparatus comprising:
   a top plate comprising a plurality of recesses arranged to form a plurality of rows extending parallel to one another; and
   a bottom plate comprising a plurality of recesses arranged to form a plurality of rows extending parallel to one another, and a plurality of channels extending perpendicularly to the plurality of rows of the bottom plate;
   wherein the top plate and the bottom plate are assembled together so that the top plate is on top of the bottom plate and the recesses of the top plate communicate with the recesses of the bottom plate so as to form a plurality of rows;
   wherein at least one of the top plate and the bottom plate is configured to slide relative to the other of the top plate and the bottom plate in order to form a plurality of columns, with each of the plurality of columns in communication with each of the plurality of channels; and
   wherein the recesses in the top plate and the recesses in the bottom plate extend at a 45 degree angle relative to the axis of a row.

2. Apparatus according to claim 1 wherein the top plate is transparent.

3. Apparatus according to claim 1 wherein at least one of the plurality of rows formed in the top plate comprises an inlet and an outlet.

4. Apparatus according to claim 1 wherein each of the plurality of channels is connected to a recess formed in the bottom plate.

5. Apparatus according to claim 1 further comprising a protein-specific antibody bound in at least one recess forming one of the plurality of rows of the top plate.

6. Apparatus according to claim 5 further comprising a sample positioned in the at least one recess containing the protein-specific antibody.

7. Apparatus according to claim 6 further comprising a catalase positioned in the at least one recess containing the protein-specific antibody and the sample.

8. Apparatus according to claim 5 further comprising a plurality of protein-specific antibodies each bound in a separate recess forming one of plurality of rows of the top plate.

9. Apparatus according to claim 8 further comprising a sample positioned in each recess containing a protein-specific antibody.

10. Apparatus according to claim 5 further comprising hydrogen peroxide positioned in a recess in a row adjacent to the row containing the protein-specific antibody.

11. Apparatus according to claim 5 further comprising ink positioned in a recess in a row adjacent to the plurality of channels.

12. Apparatus according to claim 1 further comprising a bar code reader for detecting the longitudinal position of ink contained in the plurality of channels.

13. A method for determining the quantity of a target protein and other types of biomarkers or analytes present in a sample, the method comprising:
   providing an apparatus comprising:
      a top plate comprising a plurality of recesses arranged to form a plurality of rows extending parallel to one another; and a bottom plate comprising a plurality of recesses arranged to form a plurality of rows extending parallel to one another, and a plurality of channels extending perpendicularly to the plurality of rows of the bottom plate;

wherein the top plate and the bottom plate are assembled together so that the top plate is on top of the bottom plate and the recesses of the top plate communicate with the recesses of the bottom plate so as to form a plurality of rows;

wherein at least one of the top plate and the bottom plate is configured to slide relative to the other of the top plate and the bottom plate in order to form a plurality of columns, with each of the plurality of columns in communication with each of the plurality of channels; and wherein the recesses in the top plate and the recesses in the bottom plate extend at a 45 degree angle relative to the axis of a row;

binding a protein-specific antibody in at least one recess forming one of the plurality of rows of the top plate;

positioning hydrogen peroxide in a recess adjacent to the row containing the protein-specific antibody;

positioning ink in a recess in a row adjacent to the plurality of channels;

positioning a sample in the at least one recess containing the protein-specific antibody;

positioning a catalase in the at least one recess containing the protein-specific antibody and the sample;

sliding one of the top plate and the bottom plate relative to the other of the top plate and the bottom plate so as to form the plurality of columns, with each column being in communication with one of the plurality of channels; and determining the quantity of the target protein and other biomarker or other molecular analyte present in the sample by detecting the longitudinal position of the ink contained in the plurality of channels.

14. A method according to claim 13 wherein the top plate is transparent.

15. A method according to claim 13 wherein at least one of the plurality of rows formed in the top plate comprises an inlet and an outlet.

16. A method according to claim 13 wherein the recesses in the top plate and the recesses in the bottom plate extend at a 45 degree angle relative to the axis of a row.

17. A method according to claim 13 wherein each of the plurality of channels is connected to a recess formed in the bottom plate.

18. A method according to claim 13 further comprising a plurality of protein-specific antibodies each bound in a separate recess forming one of the plurality of rows of the top plate.

19. A method according to claim 13 further comprising using a bar code reader to detect the longitudinal position of ink contained in the plurality of channels.

20. A method for determining the quantity of a target analyte present in a sample, the method comprising:

providing an apparatus comprising:

a top plate comprising a plurality of recesses arranged to form a plurality of rows extending parallel to one another; and a bottom plate comprising a plurality of recesses arranged to form a plurality of rows extending parallel to one another, and a plurality of channels extending perpendicularly to the plurality of rows of the bottom plate;

wherein the top plate and the bottom plate are assembled together so that the top plate is on top of the bottom plate and the recesses of the top plate communicate with the recesses of the bottom plate so as to form a plurality of rows;

wherein at least one of the top plate and the bottom plate is configured to slide relative to the other of the top plate and the bottom plate in order to form a plurality of columns, with each of the plurality of columns in communication with each of the plurality of channels; and wherein the recesses in the top plate and the recesses in the bottom plate extend at a 45 degree angle relative to the axis of a row;

binding a capture agent in at least one recess forming one of the plurality of rows of the top plate, introducing a sample into the at least one recess so that an analyte contained in the sample is bound to the capture agent, and binding a probe to the bound analyte; and positioning a reagent in a recess adjacent to the row containing the capture agent, bound analyte and bound probe; and positioning ink in a recess in a row adjacent to the plurality of channels;

sliding one of the top plate and the bottom plate relative to the other of the top plate and the bottom plate so as to form the plurality of columns, with each column being in communication with one of the plurality of channels; and determining the quantity of the analyte present in the sample by detecting the longitudinal position of the ink contained in the plurality of channels.

21. A method according to claim 20 wherein the probe and reagent are selected from the group consisting of catalase and hydrogen peroxide, platinum film or particles and hydrogen peroxide, catalase and carbamide peroxide, zinc and chloric acid and iron and chloric acid.

22. Apparatus according to claim 1 further comprising an ELISA probe to react with a reagent to generate gas.

23. Apparatus according to claim 22 wherein the ELISA probe and reagent are selected from the group consisting of catalase and hydrogen peroxide, platinum film or particles and hydrogen peroxide, catalase and carbamide peroxide, zinc and chloric acid and iron and chloric acid.

24. A method according to claim 13 wherein advancement of the ink contained in the plurality of channels indicates the quantity of the target protein or other biomarker or other molecular analyte present in the sample.

25. Apparatus according to claim 1 wherein advancement of an ink contained in the plurality of channels indicates the quantity of the target protein or other biomarker or other molecular analyte present in the sample.

26. Method according to claim 20 wherein advancement of the ink contained in the plurality of channels indicates the quantity of the analyte present in the sample.

27. Apparatus according to claim 1 wherein the top plate and the bottom plate are made from a material selected from the group consisting of glass, silicon, plastics, ceramics, quartz and metal oxide.

28. Method according to claim 13 wherein the top plate and the bottom plate are made from a material selected from the group consisting of glass, silicon, plastics, ceramics, quartz and metal oxide.

29. Method according to claim 20 wherein the top plate and the bottom plate are made from a material selected from the group consisting of glass, silicon, plastics, ceramics, quartz and metal oxide.

30. Apparatus according to claim 1 wherein the plurality of columns in communication with the plurality of channels form a readout panel for determining the quantity of the target protein and other types of biomarkers or analytes present in the sample.

31. A method according to claim 13 wherein the plurality of columns in communication with the plurality of channels form a readout panel for determining the quantity of the target protein and other types of biomarkers or analytes present in the sample.

32. A method according to claim 20 wherein the plurality of columns in communication with the plurality of channels form a readout panel for determining the quantity of the analyte present in the sample.

33. A method according to claim 20 wherein the bound analyte and probe form an assay sandwich, and the assay sandwich is formed by one selected from the group consisting of ELISA, nucleic acid hybridization, hydrogen bonding, electrostatic reaction and formation of covalent bond.

34. Apparatus according to claim 1 further comprising an assay and a probe bound in at least one recess forming one of the plurality of rows of the top plate.

35. Apparatus according to claim 34 wherein the assay and the probe form an assay sandwich, and the assay sandwich is formed by one selected from the group consisting of ELISA, nucleic acid hybridization, hydrogen bonding, electrostatic reaction and formation of covalent bond.

36. Apparatus according to claim 1 wherein the target protein, biomarker or analyte present in a sample is selected from the group consisting of a protein, a nucleic acid, a peptide, a sugar, an organic compound, a polymer, a metal ion, bacteria, cells and particles.

37. A method according to claim 13 wherein the target protein, biomarker or analyte present in a sample is selected from the group consisting of a protein, a nucleic acid, a peptide, a sugar, an organic compound, a polymer, a metal ion, bacteria, cells and particles.

38. A method according to claim 20 wherein the target analyte present in a sample is selected from the group consisting of a protein, a nucleic acid, a peptide, a sugar, an organic compound, a polymer, a metal ion, bacteria, cells and particles.

39. Apparatus according to claim 1 further comprising:
   a capture agent bound in at least one recess forming one of the plurality of rows of the top plate, a sample comprising at least one analyte, the analyte being bound to the capture agent, and a probe bound to the bound analyte;
   a reagent positioned in at least one recess in a row adjacent to the row containing the capture agent, the bound analyte and the bound probe, wherein reaction of the reagent with the probe produces a gas in a quantity reflective of the quantity of the analyte present in the sample; and
   ink positioned in a row adjacent to the plurality of channels.

40. Apparatus according to claim 39 wherein the reagent is positioned in a plurality of rows, with one row being adjacent to the row containing the capture agent, the bound analyte and the bound probe, and with the remainder of the rows containing the reagent alternating with rows containing an amplifier agent, wherein reaction of the reagent with the amplifier agent produces a gas in a quantity larger than, but proportional to, the quantity of gas produced by the reaction of the reagent with the probe.

41. A method according to claim 20 wherein reaction of the reagent with the probe produces a gas in a quantity reflective of the quantity of the analyte present in the sample, and further wherein the reagent is positioned in a plurality of rows, with one row being adjacent to the row containing the capture agent, the bound analyte and the bound probe, and with the remainder of the rows containing the reagent alternating with rows containing an amplifier agent, wherein reaction of the reagent with the amplifier agent produces a gas in a quantity larger than, but proportional to, the quantity of gas produced by the reaction of the reagent with the probe.

42. Apparatus according to claim 1 further comprising a capture agent bound in at least one recess forming one of the plurality of rows of the top plate.

43. Apparatus according to claim 42 further comprising a sample comprising at least one analyte and a probe.

44. Apparatus for determining the quantity of a target protein and other types of biomarkers or analytes present in a sample, the apparatus comprising:
   a top plate comprising a plurality of recesses arranged to form a plurality of rows extending parallel to one another; and
   a bottom plate comprising a plurality of recesses arranged to form a plurality of rows extending parallel to one another, and a plurality of channels extending perpendicularly to the plurality of rows of the bottom plate;
   wherein the top plate and the bottom plate are assembled together so that the top plate is on top of the bottom plate and the recesses of the top plate communicate with the recesses of the bottom plate so as to form a plurality of rows;
   wherein at least one of the top plate and the bottom plate is configured to slide relative to the other of the top plate and the bottom plate in order to form a plurality of columns, with each of the plurality of columns in communication with each of the plurality of channels; and
   wherein each of the plurality of channels is connected to a recess formed in the bottom plate.

45. Apparatus according to claim 44 wherein the top plate is transparent.

46. Apparatus according to claim 44 wherein at least one of the plurality of rows formed in the top plate comprises an inlet and an outlet.

47. Apparatus according to claim 44 wherein the recesses in the top plate and the recesses in the bottom plate extend at a 45 degree angle relative to the axis of a row.

48. Apparatus according to claim 44 further comprising a protein-specific antibody bound in at least one recess forming one of the plurality of rows of the top plate.

49. Apparatus according to claim 48 further comprising a sample positioned in the at least one recess containing the protein-specific antibody.

50. Apparatus according to claim 49 further comprising a catalase positioned in the at least one recess containing the protein-specific antibody and the sample.

51. Apparatus according to claim 48 further comprising a plurality of protein-specific antibodies each bound in a separate recess forming one of the plurality of rows of the top plate.

52. Apparatus according to claim 51 further comprising a sample positioned in each recess containing a protein-specific antibody.

53. Apparatus according to claim 48 further comprising hydrogen peroxide positioned in a recess in a row adjacent to the row containing the protein-specific antibody.

54. Apparatus according to claim 48 further comprising ink positioned in a recess in a row adjacent to the plurality of channels.

55. Apparatus according to claim 44 further comprising a bar code reader for detecting the longitudinal position of ink contained in the plurality of channels.

56. A method for determining the quantity of a target protein and other types of biomarkers or analytes present in a sample, the method comprising:
   providing an apparatus comprising:
      a top plate comprising a plurality of recesses arranged to form a plurality of rows extending parallel to one another; and
      a bottom plate comprising a plurality of recesses arranged to form a plurality of rows extending parallel to one another, and a plurality of channels extending perpendicularly to the plurality of rows of the bottom plate;
      wherein the top plate and the bottom plate are assembled together so that the top plate is on top of the bottom plate and the recesses of the top plate communicate with the recesses of the bottom plate so as to form a plurality of rows;
      wherein at least one of the top plate and the bottom plate is configured to slide relative to the other of the top plate and the bottom plate in order to form a plurality of columns, with each of the plurality of columns in communication with each of the plurality of channels; and
      wherein each of the plurality of channels is connected to a recess formed in the bottom plate;
   binding a protein-specific antibody in at least one recess forming one of the plurality of rows of the top plate;
   positioning hydrogen peroxide in a recess adjacent to the row containing the protein-specific antibody;
   positioning ink in a recess in a row adjacent to the plurality of channels;
   positioning a sample in the at least one recess containing the protein-specific antibody;
   positioning a catalase in the at least one recess containing the protein-specific antibody and the sample;
   sliding one of the top plate and the bottom plate relative to the other of the top plate and the bottom plate so as to form the plurality of columns, with each column being in communication with one of the plurality of channels; and
   determining the quantity of the target protein and other biomarker or other molecular analyte present in the sample by detecting the longitudinal position of the ink contained in the plurality of channels.

57. A method according to claim 56 wherein the top plate is transparent.

58. A method according to claim 56 wherein at least one of the plurality of rows formed in the top plate comprises an inlet and an outlet.

59. A method according to claim 56 wherein the recesses in the top plate and the recesses in the bottom plate extend at a 45 degree angle relative to the axis of a row.

60. A method according to claim 56 wherein each of the plurality of channels is connected to a recess formed in the bottom plate.

61. A method according to claim 56 further comprising a plurality of protein-specific antibodies each bound in a separate recess forming one of the plurality of rows of the top plate.

62. A method according to claim 56 further comprising using a bar code reader to detect the longitudinal position of ink contained in the plurality of channels.

63. A method for determining the quantity of a target analyte present in a sample, the method comprising:
   providing an apparatus comprising:
      a top plate comprising a plurality of recesses arranged to form a plurality of rows extending parallel to one another; and
      a bottom plate comprising a plurality of recesses arranged to form a plurality of rows extending parallel to one another, and a plurality of channels extending perpendicularly to the plurality of rows of the bottom plate;
      wherein the top plate and the bottom plate are assembled together so that the top plate is on top of the bottom plate and the recesses of the top plate communicate with the recesses of the bottom plate so as to form a plurality of rows;
      wherein at least one of the top plate and the bottom plate is configured to slide relative to the other of the top plate and the bottom plate in order to form a plurality of columns, with each of the plurality of columns in communication with each of the plurality of channels; and
      wherein each of the plurality of channels is connected to a recess formed in the bottom plate;
   binding a capture agent in at least one recess forming one of the plurality of rows of the top plate, introducing a sample into the at least one recess so that an analyte contained in the sample is bound to the capture agent, and binding a probe to the bound analyte; and positioning a reagent in a recess adjacent to the row containing the capture agent, bound analyte and bound probe; and positioning ink in a recess in a row adjacent to the plurality of channels;
   sliding one of the top plate and the bottom plate relative to the other of the top plate and the bottom plate so as to form the plurality of columns, with each column being in communication with one of the plurality of channels; and
   determining the quantity of the analyte present in the sample by detecting the longitudinal position of the ink contained in the plurality of channels.

64. A method according to claim 63 wherein the probe and reagent are selected from the group consisting of catalase and hydrogen peroxide, platinum film or particles and hydrogen peroxide, catalase and carbamide peroxide, zinc and chloric acid and iron and chloric acid.

65. Apparatus according to claim 44 further comprising an ELISA probe to react with a reagent to generate gas.

66. Apparatus according to claim 65 wherein the ELISA probe and reagent are selected from the group consisting of catalase and hydrogen peroxide, platinum film or particles and hydrogen peroxide, catalase and carbamide peroxide, zinc and chloric acid and iron and chloric acid.

67. A method according to claim 56 wherein advancement of the ink contained in the plurality of channels indicates the quantity of the target protein or other biomarker or other molecular analyte present in the sample.

68. Apparatus according to claim 44 wherein advancement of an ink contained in the plurality of channels indicates the quantity of the target protein or other biomarker or other molecular analyte present in the sample.

69. Method according to claim 63 wherein advancement of the ink contained in the plurality of channels indicates the quantity of the analyte present in the sample.

70. Apparatus according to claim 44 wherein the top plate and the bottom plate are made from a material selected from the group consisting of glass, silicon, plastics, ceramics, quartz and metal oxide.

71. Method according to claim 56 wherein the top plate and the bottom plate are made from a material selected from the group consisting of glass, silicon, plastics, ceramics, quartz and metal oxide.

72. Method according to claim 63 wherein the top plate and the bottom plate are made from a material selected from the group consisting of glass, silicon, plastics, ceramics, quartz and metal oxide.

73. Apparatus according to claim 44 wherein the plurality of columns in communication with the plurality of channels form a readout panel for determining the quantity of the target protein and other types of biomarkers or analytes present in the sample.

74. A method according to claim 56 wherein the plurality of columns in communication with the plurality of channels form a readout panel for determining the quantity of the target protein and other types of biomarkers or analytes present in the sample.

75. A method according to claim 63 wherein the plurality of columns in communication with the plurality of channels form a readout panel for determining the quantity of the analyte present in the sample.

76. A method according to claim 63 wherein the bound analyte and probe form an assay sandwich, and the assay sandwich is formed by one selected from the group consisting of ELISA, nucleic acid hybridization, hydrogen bonding, electrostatic reaction and formation of covalent bond.

77. Apparatus according to claim 44 further comprising an assay and a probe bound in at least one recess forming one of the plurality of rows of the top plate.

78. Apparatus according to claim 77 wherein the assay and the probe form an assay sandwich, and the assay sandwich is formed by one selected from the group consisting of ELISA, nucleic acid hybridization, hydrogen bonding, electrostatic reaction and formation of covalent bond.

79. Apparatus according to claim 44 wherein the target protein, biomarker or analyte present in a sample is selected from the group consisting of a protein, a nucleic acid, a peptide, a sugar, an organic compound, a polymer, a metal ion, bacteria, cells and particles.

80. A method according to claim 56 wherein the target protein, biomarker or analyte present in a sample is selected from the group consisting of a protein, a nucleic acid, a peptide, a sugar, an organic compound, a polymer, a metal ion, bacteria, cells and particles.

81. A method according to claim 63 wherein the target analyte present in a sample is selected from the group consisting of a protein, a nucleic acid, a peptide, a sugar, an organic compound, a polymer, a metal ion, bacteria, cells and particles.

82. Apparatus according to claim 44 further comprising:
a capture agent bound in at least one recess forming one of the plurality of rows of the top plate, a sample comprising at least one analyte, the analyte being bound to the capture agent, and a probe bound to the bound analyte;
a reagent positioned in at least one recess in a row adjacent to the row containing the capture agent, the bound analyte and the bound probe, wherein reaction of the reagent with the probe produces a gas in a quantity reflective of the quantity of the analyte present in the sample; and
ink positioned in a row adjacent to the plurality of channels.

83. Apparatus according to claim 82 wherein the reagent is positioned in a plurality of rows, with one row being adjacent to the row containing the capture agent, the bound analyte and the bound probe, and with the remainder of the rows containing the reagent alternating with rows containing an amplifier agent, wherein reaction of the reagent with the amplifier agent produces a gas in a quantity larger than, but proportional to, the quantity of gas produced by the reaction of the reagent with the probe.

84. A method according to claim 63 wherein reaction of the reagent with the probe produces a gas in a quantity reflective of the quantity of the analyte present in the sample, and further wherein the reagent is positioned in a plurality of rows, with one row being adjacent to the row containing the capture agent, the bound analyte and the bound probe, and with the remainder of the rows containing the reagent alternating with rows containing an amplifier agent, wherein reaction of the reagent with the amplifier agent produces a gas in a quantity larger than, but proportional to, the quantity of gas produced by the reaction of the reagent with the probe.

85. Apparatus according to claim 44 further comprising a capture agent bound in at least one recess forming one of the plurality of rows of the top plate.

86. Apparatus according to claim 85 further comprising a sample comprising at least one analyte and a probe.

* * * * *